United States Patent
Fanson

(10) Patent No.: US 11,087,963 B2
(45) Date of Patent: Aug. 10, 2021

(54) IN-VEHICLE BIOCHEMICAL SENSORS

(71) Applicant: Toyota Motor Engineering & Manufacturing North America, Inc., Plano, TX (US)

(72) Inventor: Paul Timothy Fanson, Howell, MI (US)

(73) Assignee: Toyota Motor Engineering & Manufacturing North America, Inc., Plano, TX (US)

( * ) Notice: Subject to any disclaimer, the term of this patent is extended or adjusted under 35 U.S.C. 154(b) by 578 days.

(21) Appl. No.: 16/035,960

(22) Filed: Jul. 16, 2018

(65) Prior Publication Data

US 2020/0020514 A1 Jan. 16, 2020

(51) Int. Cl.
*H01J 49/00* (2006.01)
*G01N 30/72* (2006.01)
*G01N 30/88* (2006.01)
*G01N 30/00* (2006.01)

(52) U.S. Cl.
CPC ...... *H01J 49/0022* (2013.01); *G01N 30/7206* (2013.01); *G01N 2030/0095* (2013.01); *G01N 2030/8881* (2013.01)

(58) Field of Classification Search
CPC ............ H01J 49/0022; G01N 30/7206; G01N 2030/8881; G01N 2030/0095; G01N 2030/884; G01N 33/497
See application file for complete search history.

(56) References Cited

U.S. PATENT DOCUMENTS

| | | | |
|---|---|---|---|
| 6,073,499 A | 6/2000 | Settles | |
| 6,885,440 B2 | 4/2005 | Silcott et al. | |
| 7,483,805 B2 | 1/2009 | Sparks et al. | |
| 9,696,311 B2 | 7/2017 | Haick et al. | |
| 2009/0321623 A1* | 12/2009 | Ross | C09D 11/037 250/271 |
| 2010/0198521 A1 | 8/2010 | Haick | |
| 2015/0226722 A1* | 8/2015 | Sengupta | G01N 21/31 506/12 |
| 2016/0361972 A1 | 12/2016 | Blackley | |
| 2019/0100791 A1* | 4/2019 | Weber | C12Q 1/68 |

OTHER PUBLICATIONS

Chutjian et al., "Overview of the Vehicle Cabin Atmosphere Monitor, a Miniature Gas Chromatograph/Mass Spectrometer for Trace Contamination Monitoring on the ISS and CEV," Research Gate, 1-5 (2007).
Lilienthal et al., "Airborne Chemical Sensing with Mobile Robots," Sensors, vol. 6, 1616-1678 (2006).
Scutti, "Experimental technology can 'smell' disease on your breath", CNN, published Nov. 7, 2017 (6 pages).

* cited by examiner

*Primary Examiner* — Nicole M Ippolito
(74) *Attorney, Agent, or Firm* — Christopher G. Darrow; Darrow Mustafa PC

(57) ABSTRACT

The devices, systems, and methods described herein generally relate to chemical profiling of an occupant in a vehicle. The devices, systems and methods described herein can detect enclosure-related chemicals, the enclosure-related chemicals including biochemicals expelled by one or more occupants. The enclosure-related chemicals can then be associated to an associated occupant of the one or more occupants. A biological profile can then be created for the associated occupant, the biological profile comprising medical information and historical information related to the enclosure-related chemicals.

20 Claims, 8 Drawing Sheets

IN-VEHICLE BIOCHEMICAL SENSORS

TECHNICAL FIELD

The subject matter described herein generally relates to biochemical sensors and, more particularly, vehicles having biochemical sensors disposed therein.

BACKGROUND

The detection, identification and quantification of target molecules in a sample has a wide variety of applications in many fields. For example, in medical diagnostics significant information can be gathered by screening bodily fluids, such as blood, for the presence of particular targets that may be indicative of a disease or disorder. In other areas, such as bioterror and environmental remediation, it is important to be able to identify the presence of toxic compounds or infectious agents in the environment. Detectors for identifying targets of interest may be based on or related to a variety of principles, such as peak absorbance of specific molecules, transistor principles used for electronic devices in integrated circuits, immunological assay, or others.

SUMMARY

Disclosed herein is an in-vehicle biochemical sensor and systems for personalized biochemical profiling of passengers in a vehicle. In one embodiment, an occupant bioprofiling system for determining biological aspects of occupants is disclosed. The occupant bioprofiling system can include one or more processors and a memory communicably coupled to the one or more processors. The memory can store instructions to a biochemical detection module including instructions that when executed by the one or more processors cause the one or more processors to detect enclosure-related chemicals in an enclosure sample, the enclosure-related chemicals including biochemicals expelled by one or more occupants, and to collect one or more detectable markers for one or more of the enclosure-related chemicals. The memory can further store instructions to an association module including instructions that when executed by the one or more processors cause the one or more processors to correlate, using the detectable markers, one or more of the enclosure-related chemicals to an associated occupant of the one or more occupants. The memory can further store instructions to a profiling module including instructions that when executed by the one or more processors cause the one or more processors to create a biological profile for the associated occupant, the biological profile comprising occupant-specific information derived from the enclosure-related chemicals.

In another embodiment, a bioprofiling vehicle is disclosed. The bioprofiling vehicle can include an air handling system and a chemical detection device in fluid communication with the air handling system. The chemical detection device can be configured to detect enclosure-related chemicals in an enclosure sample, the enclosure-related chemicals including biochemicals expelled by one or more occupants. The chemical detection device can be further configured to collect one or more detectable markers for one or more of the enclosure-related chemicals. The chemical detection device can be further configured to correlate, using the detectable markers, one or more of the enclosure-related chemicals to an associated occupant of the one or more occupants. The chemical detection device can be further configured to create a biological profile for the associated occupant, the biological profile comprising occupant-specific information derived from the enclosure-related chemicals.

In another embodiment, a non-transitory computer-readable medium for determining biological aspects of occupants is disclosed. The non-transitory computer-readable medium can store instructions that when executed by one or more processors cause the one or more processors to detect enclosure-related chemicals in an enclosure sample, the enclosure-related chemicals including biochemicals expelled by one or more occupants. The non-transitory computer-readable medium can further store instructions to collect one or more detectable markers for one or more of the enclosure-related chemicals. The non-transitory computer-readable medium can further store instructions to correlate, using the detectable markers, one or more of the enclosure-related chemicals to an associated occupant of the one or more occupants. The non-transitory computer-readable medium can further store instructions to create a biological profile for the associated occupant, the biological profile comprising occupant-specific information derived from the enclosure-related chemicals.

BRIEF DESCRIPTION OF THE DRAWINGS

So that the manner in which the above recited features of the present disclosure can be understood in detail, a more particular description of the disclosure, briefly summarized above, may be had by reference to the embodiments, some of which are illustrated in the appended drawings. It is to be noted, however, that the appended drawings illustrate only typical embodiments of this disclosure and are therefore not to be considered limiting of its scope. The disclosure may admit to other equally effective embodiments.

To facilitate understanding, identical reference numerals have been used, wherever possible, to designate identical elements that are common to the figures. Additionally, elements of one embodiment may be advantageously adapted for utilization in other embodiments described herein.

DETAILED DESCRIPTION

Figure 1:
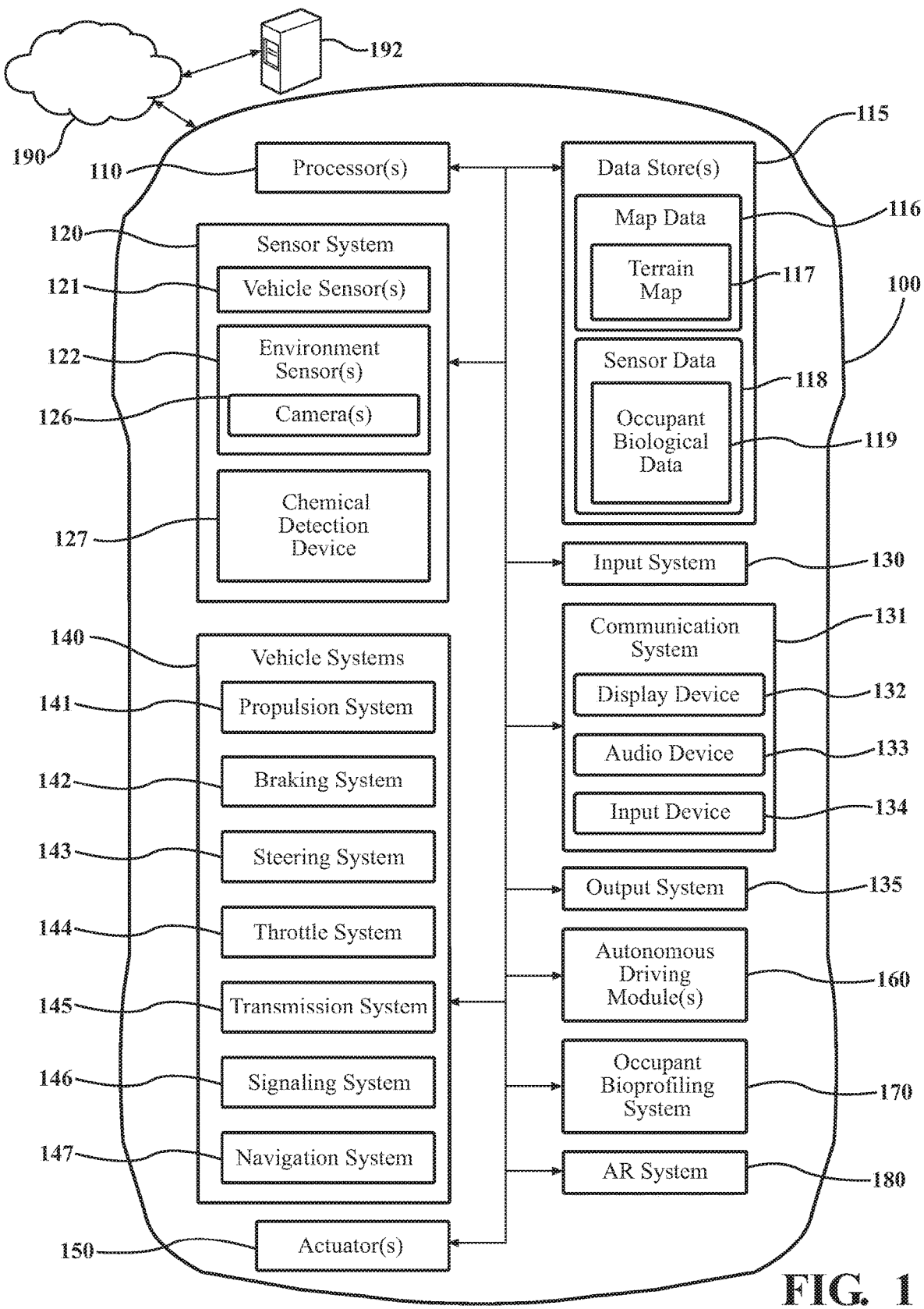
FIG. 1 is a block diagram of a vehicle with an in-vehicle biochemical sensor usable as part of an occupant bioprofiling system, according to embodiments described herein.

Embodiments described herein disclose in-vehicle biochemical sensors, and systems and methods of use. The embodiments described herein include integrating one or more biochemical sensors. The biochemical sensors, as disclosed herein, can detect biochemicals expelled by an occupant, such as airborne molecules of a driver and passengers inside a vehicle, through the air handling system. As such, the devices, systems, and methods disclosed here are able to monitor for the presence of homeostatic changes in the occupant, such as disease or drug/alcohol, by detecting biochemicals having unique profile signatures. Furthermore, the occupants, such as the vehicle driver and or passengers, may spend a fixed amount of time in the closed volume of the vehicle in each day or week. As such, the disclosed embodiments provide a unique opportunity to collect and process this data and build an accurate health profile, an early disease detection profile, or detect other changes in homeostasis of the occupant. If a negative change is detected, the embodiments described herein can provide an indication, such as warning the driver. If the deleterious change is believed to impair the occupant's capability to perform desired tasks, the devices, systems and methods can take further precautions to protect the vehicle, the occupant, or both, such as warning the driver and/or locking the vehicle from operation.

The embodiments described herein can include using one or more micro channel devices (e.g., Gas Chromatographs, Mass Spectrometers) as part of the biochemical sensors. The micro channel devices can be located inside the vehicle, such that the biochemical sensors can monitor expelled biochemicals, such as airborne particles and molecules. Further embodiments can include biochemical sensors that monitor expelled chemicals (e.g., breath analysis) related to one or more disease states. The embodiments described herein can include creating a medical profile for each occupant based on chemical analysis. If any chemicals or chemical changes are detected having a profile signature associated with certain diseases or conditions (e.g., cancer, heart disease, kidney disease, liver disease, pregnancy, fertility windows, etc.) the user or others can be notified and chemical readings can be noted as part of an occupant bioprofile through the embodiments described herein.

In further embodiments, the systems, devices and methods can also create an occupant-specific bioprofile. The occupant-specific bioprofile can include personalized detections, such as which occupant the alcohol/disease was detected from and at what levels. In one embodiment, if the driver has an alcohol level above a legal threshold, the devices, systems, and methods described herein can warn the driver through existing visual or audible notifications and disable the vehicle from being driven by that driver. If alcohol levels of a passenger (and not the driver) is detected, the devices, systems, and methods described herein can provide a communication while maintaining vehicle control with the driver, such as by warning the driver. The devices, systems, and methods described herein can include the ability to discriminate between the occupants, such as the driver and the passenger, through indirect techniques (such as pattern matching to other chemical marks in the profile) or direct techniques (such as sampling DNA). The indirect techniques can include non-invasive analysis, such as pattern matching to other chemical marks in the profile. The direct techniques can include invasive analysis or biological sample matching, such as sampling DNA. The embodiments disclosed herein are more clearly described with reference to the figures below.

Referring to FIG. 1, an example of a vehicle 100 is illustrated. As used herein, a "vehicle" is any form of motorized transport. In one or more embodiments, the vehicle 100 is an automobile. While embodiments will be described herein with respect to automobiles, it will be understood that embodiments are not limited to automobiles. In some embodiments, the vehicle 100 may be any other form of motorized transport that, for example, can include a chemical detection device. In one or more embodiments, the vehicle can further include an occupant bioprofiling system or capabilities to support an occupant bioprofiling system, and thus benefits from the functionality discussed herein. In some instances, the vehicle 100 is one that is manually driven by a driver. In other instances, the vehicle 100 is configured to switch selectively between an autonomous mode, one or more semi-autonomous operational modes, and/or a manual mode. Such switching also referred to as handover when transitioning to a manual mode can be implemented in a suitable manner, now known or later developed. "Manual mode" means that all of or a majority of the navigation and/or maneuvering of the vehicle is performed according to inputs received from a user (e.g., human driver/operator).

The vehicle 100 can include a processor 110. In one or more embodiments, the processor 110 can be a main processor of the vehicle 100. In one example, the processor 110 can be an electronic control unit (ECU). Depending on the desired configuration, the processor 110 can be of any type for use in the data processing and analysis described herein. The processor 110 can be a microprocessor (µP), a microcontroller (µC), a digital signal processor (DSP), or any combination thereof. The processor 110 can be a set of one or more processors or can be a multi-processor core, depending on the particular implementation. Further, processor 110 can be one or more heterogeneous processor systems, in which a main processor is present with secondary processors on a single chip. In another example, the processor 110 can be a symmetric multi-processor system containing multiple processors of the same type. Further combinations or permutations of the processor 110 are contemplated without specific recitation herein.

The vehicle 100 can include a data store 115. The data store 115 is any piece of hardware that is capable of storing data or information. Examples of data or information which can be stored in the data store 115 include, without limitation, data, program code in functional form, and/or other suitable information either on a temporary basis and/or a permanent basis. The data store 115 can include one or more modules that include computer-readable instructions that, when executed by the processor 110, cause the processor 110 to perform methods and functions that are discussed herein. The data store 115 can include volatile and/or non-volatile memory. An example of the data store 115 can include RAM (Random Access Memory), flash memory, ROM (Read-Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The data store 115 can be a component of the processor 110, or the data store 115 can be operably connected to the processor 110 for use thereby. The media used by data store 115 can be removable. For example, a removable hard drive can be used for data store 115. The term "operably connected," as used throughout this description, can include direct or indirect connections, including connections without direct physical contact.

In one or more embodiments, the one or more data stores 115 can include map data 116. The map data 116 can include maps of one or more geographic areas. In some instances, the map data 116 can include information or data on roads, traffic control devices, road surface markings, structures, features, and/or landmarks in the one or more geographic areas. The map data 116 can be in any suitable form. In some instances, the map data 116 can include aerial views of an area. The map data 116 can include measurements, dimensions, distances, and/or information for one or more items included in the map data 116 and/or relative to other items included in the map data 116. The map data 116 can include a digital map with information about road geometry. The map data 116 can be high quality and/or highly detailed. In one or more embodiments, the map data 116 can include one or more terrain maps 117, including information about the ground, terrain, roads, surfaces, and/or other features of one or more geographic areas.

The one or more data stores 115 can include sensor data 118. In this context, "sensor data" means any information about the sensors that the vehicle 100 is equipped with, including the capabilities and other information about such sensors. As will be explained below, the vehicle 100 can include the sensor system 120. The sensor data 118 can relate to one or more sensors of the sensor system 120. In some instances, at least a portion of the map data 116 and/or the sensor data 118 can be located in one or more data stores 115 located onboard the vehicle 100. Alternatively, or in addition, at least a portion of the map data 116 and/or the sensor data 118 can be located in one or more data stores 115 that are located remotely from the vehicle 100.

In one or more embodiments, the sensor data 118 can further include occupant biological data 119. The occupant biological data 119 can include biological information as received by one or more occupants of the vehicle 100. The occupant biological data 119 can include biochemical data regarding associated disease states, monitoring of homeostatic parameters, signs of bacterial infection/viral infection, nutrient deficiencies, or others. The occupant biological data 119 can be derived from collected information, such as through the sensor system 120, retrieved information from available sources, such as medical record information, publicly available information or combinations thereof. The occupant biological data 119 can further include toxicology profiling, including biochemical signs of substance abuse (e.g., alcohol or other illicit substances), indications of poisoning or heavy metal accumulation, and other toxicological information about the occupants.

As stated above, the occupant biological data 119 can include homeostatic parameters. Homeostatic parameters are the biologically maintained state of the various chemistries of the body. One or more of these homeostatic parameters can produce detectable differences in the biochemical expelled from the body. In the monitoring of these homeostatic parameters, temporal chemical variations such as biochemical quantities, changes, and change rates can provide indications of deleterious changes before they are detectable. Temporal chemical variations are variations in chemical quantities as a function of time or time frames. Examples of homeostatic parameters which can be monitored include detectable biomarkers of a pre-diabetic state, detectable markers of pre-ischemic conditioning which can indicate an oncoming heart attack, detectable markers of pulmonary edema for high blood pressure and cardiac hypertrophy, and others. As such, the monitoring of these homeostatic parameters over time can act as a heuristic mechanism to associate biological change with various physiological parameters.

As noted above, the vehicle 100 can include the sensor system 120. The sensor system 120 can include one or more sensors. "Sensor" means any device, component, system or combination thereof that can detect and/or sense something. The one or more sensors can be configured to detect, and/or sense in real-time. As used herein, the term "real-time" means a level of processing responsiveness that a user or system senses as sufficiently immediate for a particular process or determination to be made, or that enables the processor to keep up with some external process.

The sensor system 120 can include any suitable type of sensor. Various examples of different types of sensors will be described herein. However, it will be understood that the embodiments are not limited to the particular sensors described. The sensor system 120 can include one or more vehicle sensors 121. The vehicle sensor(s) 121 can detect, determine, and/or sense information about the vehicle 100 itself. In one or more embodiments, the vehicle sensor(s) 121 can be configured to detect, and/or sense position and orientation changes of the vehicle 100, such as, for example, based on inertial acceleration. In one or more embodiments, the vehicle sensor(s) 121 can include one or more accelerometers, one or more gyroscopes, an inertial measurement unit (IMU), a dead-reckoning system, a global navigation satellite system (GNSS), a global positioning system (GPS), a navigation system 147, and/or other suitable sensors. The vehicle sensor(s) 121 can be configured to detect, and/or sense one or more characteristics of the vehicle 100. In one or more embodiments, the vehicle sensor(s) 121 can include a speedometer to determine a current speed of the vehicle 100.

The sensor system 120 can further include one or more environment sensors 122 configured to acquire, and/or sense driving environment data. "Driving environment data" includes data or information about the external environment in which an autonomous vehicle is located or one or more portions thereof. For example, the one or more environment sensors 122 can be configured to detect, quantify and/or sense obstacles in at least a portion of the external environment of the vehicle 100 and/or information/data about such obstacles. Such obstacles may be stationary objects and/or dynamic objects. The one or more environment sensors 122 can be configured to detect, measure, quantify and/or sense other things in the external environment of the vehicle 100, such as, for example, lane markers, signs, traffic lights, traffic signs, lane lines, crosswalks, curbs proximate the vehicle 100, off-road objects, etc.

Various examples of sensors of the sensor system 120 will be described herein. The example sensors may be part of the one or more environment sensors 122 and/or the one or more vehicle sensors 121. Moreover, the sensor system 120 can include operator sensors that function to track or otherwise monitor aspects related to the driver/operator of the vehicle 100. However, it will be understood that the embodiments are not limited to the particular sensors described. As an example, in one or more embodiments, the sensor system 120 can include a variety of sensors, such as one or more cameras 126. In one or more embodiments, the one or more cameras 126 can be high dynamic range (HDR) cameras, infrared (IR) cameras and so on. In one embodiment, the cameras 126 include one or more cameras disposed within a passenger compartment of the vehicle for performing eye-tracking on the operator/driver in order to determine a gaze of the operator/driver, an eye track of the operator/driver, and so on.

In another embodiment, the sensor system 120 can include a chemical detection device 127. The chemical detection device 127 is a device capable of collecting and analyzing biochemicals available to the interior of the vehicle 100. In some embodiments, the chemical detection device 127 can be a component and/or a plurality of components which can collect and analyze enclosure-related chemicals. Enclosure-related chemicals are biologically-related organic and inorganic chemicals which are available to the interior of the vehicle 100. In some embodiments, the chemical detection device 127 can be a micro channel device, such as mass spectrometers, gas chromatographs, or other devices capable of chemical analysis. In one example, the chemical detection device 127 is a combination gas chromatograph and mass spectrometer.

The chemical detection device 127 is a device in fluid connection with the interior of the vehicle 100 which can detect and differentiate various chemistries from the vehicle interior. The chemical detection device 127 can further include real-time sampling, such that consistent measures are being made at all times. The chemical detection device 127 can further include the ability to differentiate between background chemistries and occupant chemistries, such as may occur due to infestation or bacterial growth in the vehicle 100. The chemical detection device 127 can be in connection with the interior of the vehicle, such as by fluid communication with an air handling system 148 of the vehicle 100. The air handling system 148 is the portion of the vehicle 100 which controls ventilation and atmospheric control of the interior of the vehicle 100. The chemical detection device 127 can further include sample collection or sample concentration, such that biological samples can be further examined for trace variations or can be examined at a later time.

The vehicle 100 can also include an input system 130. An "input system" includes any device, component, system, element or arrangement or groups thereof that enable information/data to be entered into a machine. The input system 130 can receive an input from a vehicle passenger (e.g. a driver or a passenger). The input system 130 can include one or more connections, either wired or wireless, for communication between other devices storing information and the vehicle 100. The input system 130 can be any suitable communication interface depending on device type and include, but is not limited to, USB (universal serial bus), frame grabber, Ethernet, or Firewire. The input system 130 can include components suitable for communication with devices, locally or remotely, such as over a network protocol (e.g., Ethernet or similar protocols). The vehicle 100 can include an output system 135. An "output system" includes any device, component, or arrangement or groups thereof that enable information/data to be presented to a vehicle passenger (e.g. a person, a vehicle passenger, etc.).

The vehicle 100 can include one or more vehicle systems 140. Various examples of the one or more vehicle systems 140 are shown in FIG. 1. However, the vehicle 100 can include more, fewer, or different vehicle systems. It should be appreciated that although particular vehicle systems are separately defined, each or any of the systems or portions thereof may be otherwise combined or segregated via hardware and/or software within the vehicle 100. The vehicle 100 can include a propulsion system 141, a braking system 142, a steering system 143, throttle system 144, a transmission system 145, a signaling system 146, and/or a navigation system 147. Each of these systems can include one or more devices, components, and/or combination thereof, now known or later developed.

The navigation system 147 can include one or more devices, sensors, applications, and/or combinations thereof, now known or later developed, configured to determine the geographic location of the vehicle 100 and/or to determine a travel route for the vehicle 100. The navigation system 147 can include one or more mapping applications to determine a travel route for the vehicle 100. The navigation system 147 can include a global positioning system, a local positioning system or a geolocation system.

The vehicle 100 further includes an occupant bioprofiling system 170 that is implemented to perform methods and other functions as disclosed herein relating to path modification and improvement based on adversarial comparison of predicted paths and actual driving paths, as provided by expert drivers. The vehicle 100 can also include a plurality of modules integrated with or interacting with the occupant bioprofiling system 170, for the comparison of driving data and environment data to the predicted path. The modules usable with the occupant bioprofiling system 170 are described with reference to FIG. 3 below.

The vehicle 100 can include one or more actuators 150. The actuators 150 can be any element or combination of elements operable to modify, adjust and/or alter one or more of the vehicle systems 140 or components thereof to responsive to receiving signals or other inputs from the processor 110 and/or the autonomous driving module(s) 160. Any suitable actuator can be used. For instance, the one or more actuators 150 can include motors, pneumatic actuators, hydraulic pistons, relays, solenoids, and/or piezoelectric actuators, just to name a few possibilities.

The vehicle 100 can include one or more modules, at least some of which are described herein. The modules can be implemented as computer-readable program code that, when executed by a processor 110, implement one or more of the various processes described herein. One or more of the modules can be a component of the processor 110, or one or more of the modules can be executed on and/or distributed among other processing systems to which the processor 110 is operably connected. The modules can include instructions (e.g., program logic) executable by one or more processor 110. Alternatively, or in addition, one or more data store 115 may contain such instructions.

In one or more embodiments, one or more of the modules described herein can include artificial or computational intelligence elements, e.g., neural network, fuzzy logic or other machine learning algorithms. Further, in one or more embodiments, one or more of the modules can be distributed among a plurality of the modules described herein. In one or more embodiments, two or more of the modules described herein can be combined into a single module.

The vehicle 100 can include one or more autonomous driving modules 160. The autonomous driving module(s) 160 can be configured to receive data from the sensor system 120, the occupant bioprofiling system 170, and/or any other type of system capable of capturing information relating to the vehicle 100 and/or the external environment of the vehicle 100. In one or more embodiments, the autonomous driving module(s) 160 can use such data to generate one or more driving scene models. The autonomous driving module(s) 160 can determine position and velocity of the vehicle 100. The autonomous driving module(s) 160 can determine the location of obstacles, or other environmental features including traffic signs, trees, shrubs, neighboring vehicles, pedestrians, etc.

The autonomous driving module(s) 160 can be configured to receive, and/or determine location information for obstacles within the external environment of the vehicle 100 for use by the processor 110, and/or one or more of the modules described herein to estimate position and orientation of the vehicle 100, vehicle position in global coordinates based on signals from a plurality of satellites, or any other data and/or signals that could be used to determine the current state of the vehicle 100 or determine the position of the vehicle 100 with respect to its environment for use in either creating a map or determining the position of the vehicle 100 in respect to map data.

The autonomous driving module(s) 160 either independently or in combination with the occupant bioprofiling system 170 can be configured to determine travel path(s), current autonomous driving maneuvers for the vehicle 100, future autonomous driving maneuvers and/or modifications to current autonomous driving maneuvers based on data acquired by the sensor system 120, driving scene models, occupant profiles, and/or data from any other suitable source. "Driving maneuver" means one or more actions that affect the movement of a vehicle. Examples of driving maneuvers include: accelerating, decelerating, braking, turning, moving in a lateral direction of the vehicle 100, changing travel lanes, merging into a travel lane, and/or reversing, just to name a few possibilities.

Figure 2A:
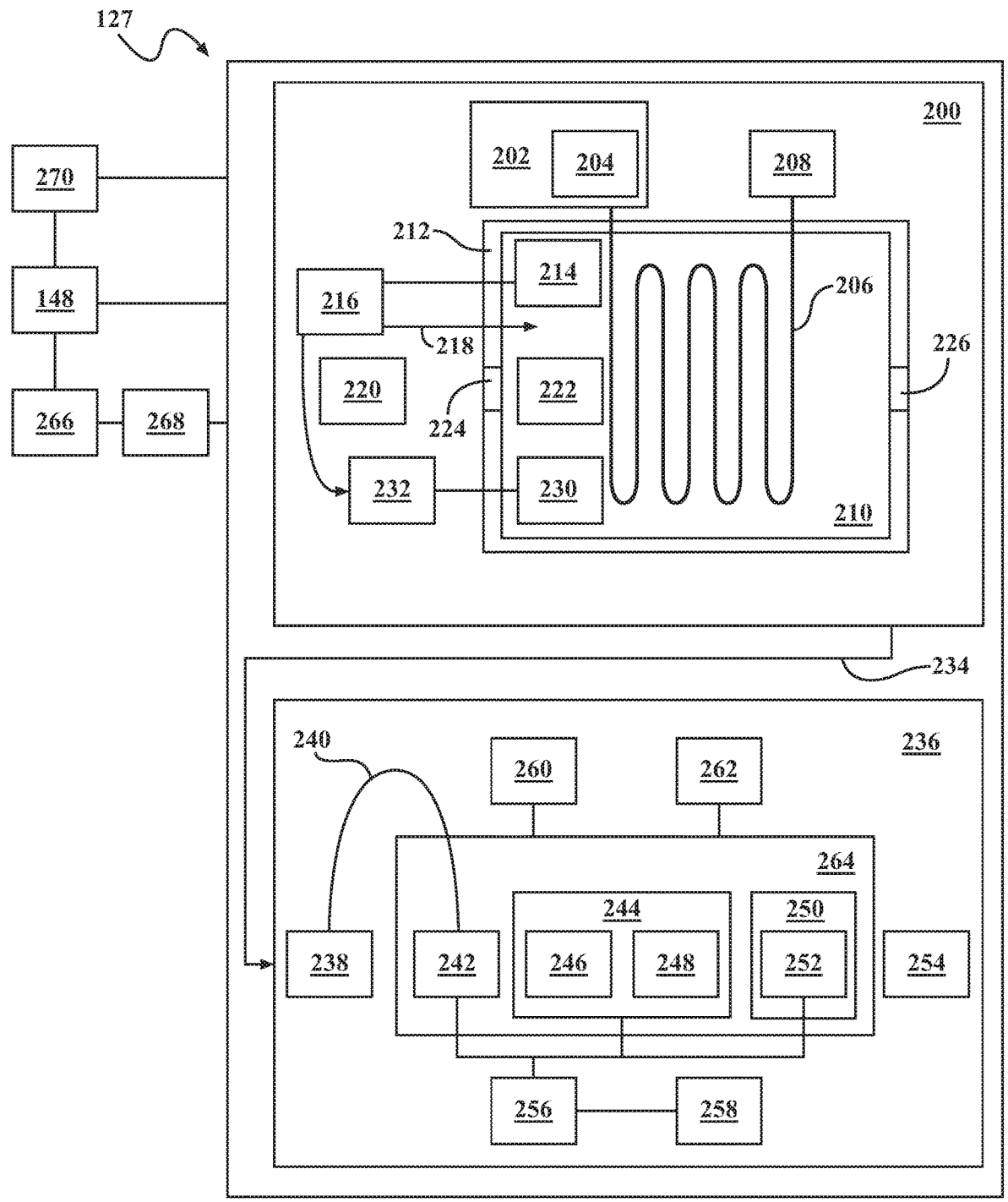
FIG. 2A is a block diagram of a chemical detection device, according to one or more embodiments.

FIG. 2A is a depiction of the chemical detection device 127. In the embodiment shown here, the chemical detection device 127 can include a combination gas chromatographic (GC) sub-assembly 200 and mass spectroscopic (MS) sub-assembly 236. The GC sub-assembly 200 is a device for separating volatile organic and inorganic components from the enclosure sample. The MS sub-assembly 236 is a device used to identify the mass-to-charge (m/Z) ratio of ions and ion fragments. The chemical detection device 127, an example of which is described here, can receive the enclosure sample from the air handling system 148 and process said enclosure sample to determine the chemical constituents of the enclosure sample. The information regarding these chemical constituents can be used to determine biological data about the source, including, but not limited to, profiling of one or more occupants, either individually or as a group.

A schematic of the GC sub-assembly 200 is shown in detail. The GC sub-assembly 200 can include a sample handler 202 and an oven 210. Sample handler 202 includes a sample source 204, a column 206, and a detector 208. Sample source 204 can further include a sample injection port, a carrier gas source, and a flow controller (not shown). The sample injection port can be hydraulically coupled to an inlet end of the column 206, while an effluent end of the column 206 is hydraulically coupled to detector 208. Oven 210 can include an insulated chamber enclosure 212, a temperature sensor 214, a ramp controller 216, a heating system 218, and a ventilation subsystem 220.

Ventilation subsystem 220 can provide ventilation to the oven 210, such as by increasing gas exchange between the cavity and the exterior environment. An air circulation device 222 can be located within oven cavity. Air circulation device 222 can circulate air within the cavity and over the column 206. When closed, ventilation subsystem 220 effects circulation with a generally direct conical flow path through chamber enclosure 212. Chamber enclosure 212 defines an oven cavity that contains column 206. The chamber enclosure 212 can include an opening through a rear face defining an intake aperture 224. The chamber enclosure 212 can be open at a front face, defining an exhaust aperture 226. A demand ramp can be selected by programming the ramp controller 216. In some embodiments, the demand ramp can include constant temperature periods and periods of constant positive slope.

The ramp controller 216 and the ventilation subsystem 220 can control temperature of the oven 210. The ramp controller 216 can be coupled to the output of the temperature sensor 214, such as for monitoring the temperature within oven cavity and/or to provide a measured temperature readout. The measured temperature can be used first to determine when to begin a ramp. Ventilation subsystem 220 can be partially open most of the time during stabilization. To adjust ventilation, ramp controller 216 controllably opens or closes the intake aperture 224 and/or the exhaust aperture 226. During a stabilization interval and before ventilation subsystem 220 is completely closed, ramp controller 216 activates current source 232, which is electrically coupled to resistive heater 230. Thus, heating begins as ventilation subsides, and is controlled and/or maintained by the same ventilation.

The positive slope portion of a heat cycle can begin with ventilation subsystem 220 closed. A heater 230, within the cavity of the oven 210, can be controlled through the ramp controller 216 to heat the chamber enclosure 212. The ventilation subsystem 220 can be controllably opened to maintain said temperature and/or minimize cool down time after an operation. Ramp controller 216 can compare measured and desired temperatures and implement error correction, such as proportional-integrated-differential error correction. If the measured temperature falls below the desired temperature, the current can be further increased. If the measured temperature rises slightly above the demand temperature, the current is reduced or turned off. If reducing heat input does not fully compensate for overheating, ventilation subsystem 220 is opened.

The GC sub-assembly 200 can progressively heat the enclosure sample through the boiling points of its components so that they can be differentially swept through a sorbent-coated column 206 by a carrier gas. Components of the enclosure sample (e.g., volatile chemicals) can then be separated according to the extent they preferentially bind to the sorbent material of the column 206. To ensure maximum resolution, spatial temperature gradients in the column 206 can be controlled. The isothermal conditions can be achieved by control of the heating system through the ramp controller 216, geometry of the oven 210, and by use of the ventilation subsystem 220, as described above. Sample components can then be detected at the detector 208 and then eluted for delivery to the MS sub-assembly 236, preservation, or disposal.

The eluted sample components can then travel through a pathway 234 to be received by the MS sub-assembly 236. The MS sub-assembly 236 can include an ion accumulation section 240, the low-resolution mass-fractionation subsection 244, and the high-resolution mass-fractionation subsection 250, each of which can be fluidly aligned to define a direction of flow for the ions being analyzed. The ion accumulation section 240 can include an ion source 238 and an ion trap 242 for production and direction of ions from the source. The low-resolution subsection 244 can include a series of linear ion trapping (LIT) regions 246, each having an axially extended trapping region surrounded by DC gate regions at opposite ends. The LIT regions 246 can further be connected by radio frequency (RF) gate regions 248. The RF gate regions 248 can generate structured RF fields to provide low-resolution, high charge capacity, and mass selectivity.

The MS sub-assembly 236 can further include a detector section 254, a set of power supplies 256, and a control system 258. The power supplies 256 can be coupled to electrodes in the ion trap 242, low-resolution mass-fractionation subsection 244, and high-resolution mass-fractionation subsection 250. Examples of available power supplies 256 include RF, alternating current (AC), and direct current (DC) sources. The control system 258 can be in communication with and control power delivery from the power supplies 256. Control system 258 can further provide a user interface for controlling the system and running automated sequences.

The ion trap 242, the low-resolution mass-fractionation subsection 244, and the high-resolution mass-fractionation subsection 250 can reside in a common vacuum housing 264. The common vacuum housing 264 can be coupled to high-vacuum pump 260 for generating low pressures. An inert gas source 262 can be coupled to the common vacuum housing 264 to introduce the inert gas and collisionally cool the ions at one or more ionization and/or detection locations, and/or to facilitate the trapped ion fragmentation. The ion source 238 can ionize the sample to be analyzed, such as a sample received from the GC sub-assembly 200. The ion source can further create an electrostatic potential, which can draw the ions produced by the source into traps or fractionation components described above.

The high-resolution mass-fractionation subsection 250 can then receive a subset of trapped ions from low-resolution mass-fractionation subsection 244. The high-resolution mass-fractionation subsection 250 can include a series of harmonic linear trapping regions (HLTs) 252, to selectively excite ions and then rotate said excited ions for selectively ejecting ions into the subsequent trap or the detector section 254. The detector section 254 can generate a signal indicative of the number and/or mass-to-charge ratio of said ions. The MS sub-assembly 236 can thus identify the mass-to-charge ratio of the ion fragments to provide information about the parent ion. The MS sub-assembly 236 can then use electric and/or magnetic fields to guide the ions fragments along trajectories that depend on their mass-to-charge ratios.

In one or more embodiments, the enclosure samples, as received from the interior of the vehicle 100, can be delivered sequentially or in tandem. In a sequential embodiment, the GC sub-assembly 200 processes the enclosure sample before delivering to the MS sub-assembly 236. In a tandem embodiment, the enclosure sample can be uniformly split such that the GC sub-assembly 200 and the MS sub-assembly 236 process separate, equivalent samples. In further embodiment, the samples can be collected for further processing, such as being delivered to an analysis location for determination of various chemistries. The order and timing of sample collection and delivery can be controlled by one or more systems of the vehicle 100, such as the occupant bioprofiling system 170.

In further embodiments, the chemical detection device 127 can further include a chemical-selective filter 266. The chemical-selective filter 266 can use properties of one or more chemicals to remove said chemical or a chemical class from the sample prior to sample processing. Weight, size, complexity, charge, reactivity or other factors of the target chemical or chemical class can be employed in capturing and removing certain chemistries from the sample. In one embodiment, the chemical-selective filter can remove chemistries that outgas from environmental objects, such as plastic objects. In another embodiment, the chemical detection device 127 can further include a biological collector 268. The biological collector 268 can be one or more devices employed to collect or concentrate samples for further processing. The biological collector 268 can be in fluid connection with the GC sub-assembly 200 and/or the MS sub-assembly 236. The biological collector 268 can gather samples, such as by compression, into one or more containers. In this way, analysis of samples can be repeated for calibration or verification purposes.

In further embodiments, the chemical detection device 127 can further include a genetic material sampler 270. The genetic material sampler 270 can collect genetic material from the one or more occupants, as delivered through the air (e.g., exhaled material) or as delivered through a given sample (e.g., saliva). In one example, the genetic material sampler 270 is a cell sorter or flow cytometry device, capable of separating cells based on cell type or morphology, expressed proteins or other factors to differentiate the source of the material. In one embodiment, the genetic material sampler 270 is a micro-fluidic cell-sorting device incorporating Laguerre-Gaussian beams of equal and opposite helical index. Once cells are sorted, the genetic material sampler 270 can store samples (e.g., biological samples) for further processing, such as cell lysis, DNA isolation, thermocycling, and sequencing. Biological samples can include biological components captured from the one or more occupants such as lost hair, excreted sweat, cell samples, or others. The biological samples can be given by the occupant or collected as discarded by the occupant.

Figure 2B:
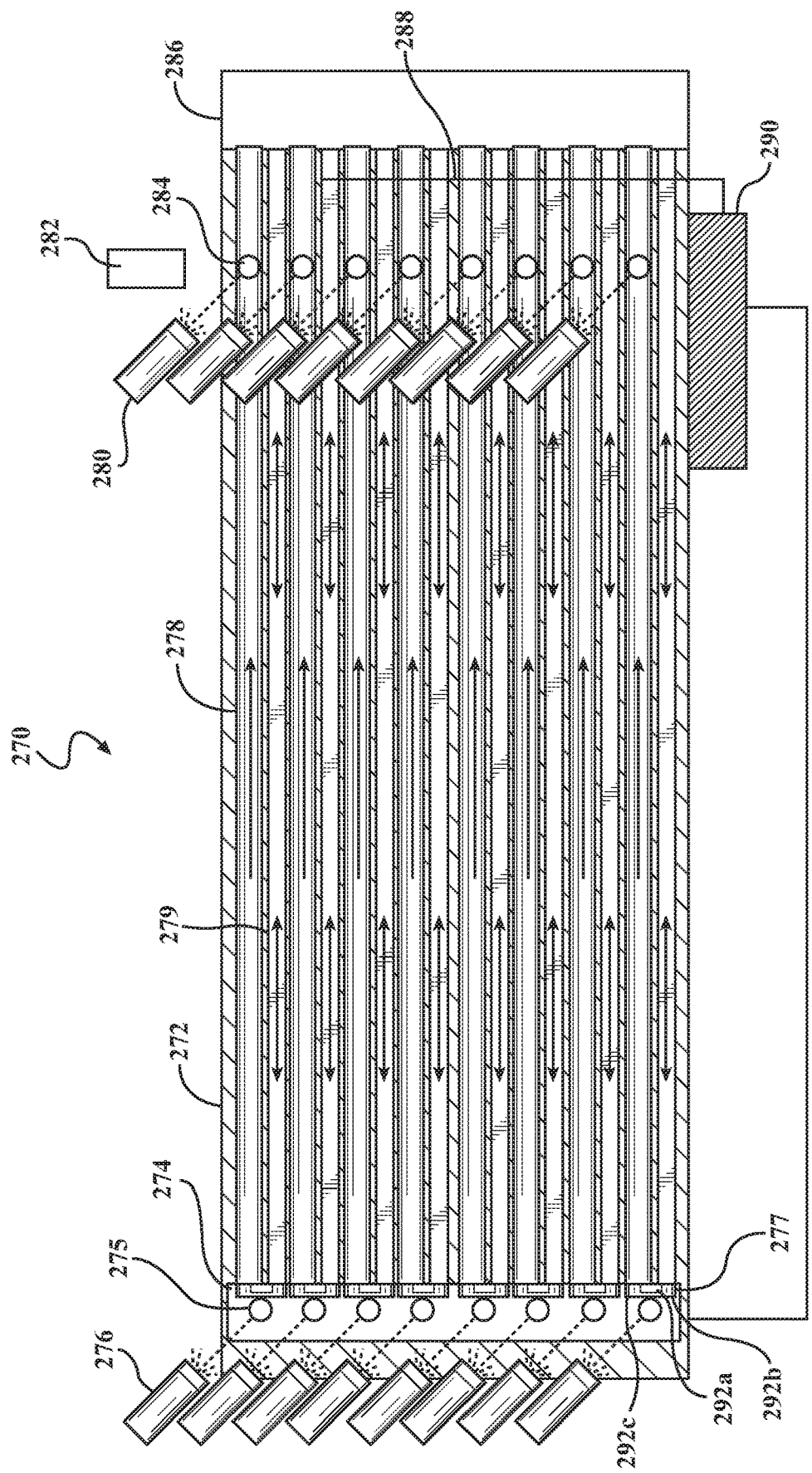
FIG. 2B depicts a genetic material sampler, according to one embodiment.

FIG. 2B depicts a genetic material sampler 270, according to one embodiment. The genetic material sampler 270 can include a substrate 272, which may have a substantially planar surface, and one or more components formed thereon or integrated therein. The substrate 272 can be composed of a semiconductor device material, such as silicon germanium, gallium arsenide, glass, sapphire or other similar materials. The genetic material sampler 270 or components thereof can have dimensions or be positioning according to need or desire of the occupant or designer.

The genetic material sampler 270 can include a sample basin 274, to receive a sample for biological material separation. The sample basin 274 can be formed on or in the substrate 272 and can be of any shape. The sample basin 274 has at least one sampling trap 275, which is the region in the sample basin 274 where the optical traps are formed, and at least one coherent radiation source 276 associated with each sampling trap 275. The sample basin 274 can be positioned and created as a flow through region for the chemical detection device. In one embodiment, the air handling system 148 delivers the collected sample through the sample basin 274, prior to the sample being received by other components of the chemical detection device 127.

The coherent radiation source 276 is a source of radiation in which the phase relationship between sections of the wave at different locations is not random, such as a laser beam. The coherent radiation source 276 can include one or more adaptive elements, such as fiber optics, spatial light modulators, mirrors, optical lenses or others, to manipulate the radiation. The coherent radiation source 276 can produce two collinear beams directed at the sampling trap radiation for the creation of optical traps at the sampling trap 275.

Optical trapping can be applied for selective filtering of cell material from the enclosure sample. Coherent radiation with a selected Gaussian intensity distribution is focused on a spherical object, such as cells from the enclosure sample, which creates a force that pushes the cell to the opposite direction due to the net dipole force. The cells eventually come to rest directly in line with the intensity maximum at the center of the beam, thus trapping the cell at the maximum of the Gaussian beam. Using two Gaussian beams converging at a point in front of the cell, the cell will be drawn to the maximum intensity point at the intersection of both beams. The two horizontal components of force can cancel, leaving a net upward vertical force until the point of convergence of the two beams reaches a point substantially near the center of the cell. Thus two beams can trap the cell in the z-direction and the x-y direction.

Optical traps, as used herein, are collinear superpositions of two Laguerre-Gaussian beams. Laguerre-Gaussian beams are Gaussian profile radiation having a screw phase angular momentum, which creates both the hollow center and the circular symmetry of the resulting beam. Laguerre-Gaussian beams thus simultaneously apply the principles of optical trapping to a donut shaped orbital beam. This optical combination traps cells with a refractive index higher than that of the surrounding medium. Collinear superposition of two Laguerre-Gaussian beams having an opposite rotation is used to prevent orbital rotation in the trapped cell.

The genetic material sampler 270 can have one or more sample channels 278 fluidly connected with the sample basin 274. The sample channels 278, shown here as eight (8) channels, is a channel having a width or a diameter which allows for intact delivery of cells in a biological sample. In one embodiment, the sample channel 278 can have a width reflecting the size of the cells to be collected, such as a diameter of less than about 50 µm, between about 10 µm and about 30 µm, or others. The sample channel 278 may have an internal and/or an external shape which is cuboid, cylindrical or other shape. The sample channel 278 may be large enough to deliver the single file line of cells surrounded by a sheath fluid. The sample channel 278 may be formed into the substrate 272 or may be positioned on the substrate 272 and of any composition stable to the described function.

The genetic material sampler 270 can further include an exhaust channel 279. The exhaust channel 279 is a channel for receiving the materials not selected during the trapping process. The exhaust channel 279 can be fluidly connected to the sample basin 274 and have dimensions, compositions and shapes as described referring to the sample channel 278. Each sample channel 278 can have a separate or shared exhaust channel 279.

The genetic material sampler 270 further includes a flow control device 277. The flow control device 277 can include devices to separate the flow of the biological sample based on trapping at the sampling trap 275, such as physical barriers, such as a microactuator with a deflection plate, or electrical deflection, such as a dielectrophoresis device. The flow control device 277 can be positioned to deflect a cell or a portion of the biological sample to either the sample channel 278 or the exhaust channel 279.

In this embodiment, the flow control device 277 is depicted as a dielectrophoresis device. The flow control device 277, positioned in front of each of the sample channel 278 and exhaust channel 279 entrances, has a positive electrode 292a and negative electrodes 292b and 292c. The positive electrode 292a provides a positive charge to all particles in the biological sample. Negative electrode 292b is on by default, so all particles are directed to the exhaust channel. When an object, such as a cell from the sample, is captured at the sampling trap 275, the capture is detected, such as by one or more radiation detection devices 282. The at least one of the radiation detection devices 282 can be optical connection with the sampling trap 275. The radiation detection devices 282 can cause the negative electrode 292c to be turned on, which will attract the positively charged particles (e.g., the cells), and move particles trapped at the sampling trap 275 down the sample channel 278.

The genetic material sampler 270 can further include a filtering trap 284 formed along the sample channel 278. The filtering trap 284 can receive radiation from a second coherent radiation source 280, such as described above with reference to the first coherent radiation source 276 for separating cells based on size. At least one of the radiation detection devices 282 can be in optical connection with the filtering traps 284 and the second coherent radiation source 280. The radiation detection device 282 may be integrated with or positioned over the substrate 272 to receive radiation delivered from the filtering trap 284.

The genetic material sampler 270 may further include a holding tank 286 and an exhaust tank 297. The holding tank 286 can be fluidly connected with the sample channel 278. The exhaust tank 297 can be fluidly connected with the exhaust channel 279. An interconnecting channel 288 may be formed between the sample channel 278 and the exhaust channel 279. The interconnecting channel 288 allows excluded portions from the biological sample, as passing through the sample channel 278, to exit the sample channel 278 and enter the exhaust channel 279 after a second separation at the filtering trap 284. The second separation offers a further opportunity to refine the biological sample.

In operation, the enclosure sample can be delivered from the air handling system 148 through the sample basin 274. The enclosure sample passes through the sampling trap 275, the sampling trap 275 selecting cells or other components which are larger than the selected size. With biological components from the occupants of the vehicle 100, such as cells, the selected size can be a diameter normally found for epithelial cells in the mouth, esophagus or lungs, such as between about 10 µm and about 30 µm. The selected or trapped cells (e.g., the biological sample) can be directed down the sample channel 278 using the flow control device 277 while the remaining portions of the enclosure sample, can be directed down the exhaust channel 279 or allowed to flow through to the remaining components of the chemical detection device 127.

The cells can be delivered single file through the sample channel 278 to the filtering traps 284 to select or filter cells based on size, luminescence or other parameters. The selected cells can be allowed to continue through the sample channel 278. The remaining components can then be redirected down the interconnecting channel 288 using a second flow control device (not shown) to the exhaust channel 279 and then the exhaust tank 297. The selected cells can then be delivered through the sample channel 278 and into the holding tank 286. The contents of the exhaust tank 297 can be processed one or more times by the same system as above to assure that all cells are collected. Once processing is complete, the sample from the holding tank 286 can be collected for further processing, such as genetic profiling, mutational or expression analysis or other processing as desired by the occupant or the occupant bioprofiling system 170.

The chemical detection device 127, as part of the vehicle 100, can detect and distinguish various chemicals from the interior of the vehicle 100. The chemical detection device 127 can communicate with the air handling system 148. The chemical detection device 127 can further be configured to detect enclosure-related chemicals, such as through the GC sub-assembly 200 and/or the MS sub-assembly 236. The enclosure-related chemicals can include organic or inorganic chemicals expelled by one or more occupants. The chemical detection device 127 can further be configured to associate one or more of the enclosure-related chemicals to an associated occupant of the one or more occupants. The chemical detection device 127 can further be configured to create a biological profile for an associated occupant. In one or more embodiments, the biological profile can include medical information and/or historical information related to the enclosure-related chemicals. The enclosure-related chemicals can be used in the detection of many issues related to the occupants of the vehicle. In one embodiment, the chemical detection device 127 can detect specific biochemicals related to disease states for individual passengers. In another embodiment, the chemical detection device 127 can detect poisons or toxins in the environment. In another example, the chemical detection device 127 can determine biochemical changes as they temporally relate to environmental changes.

Figure 3:
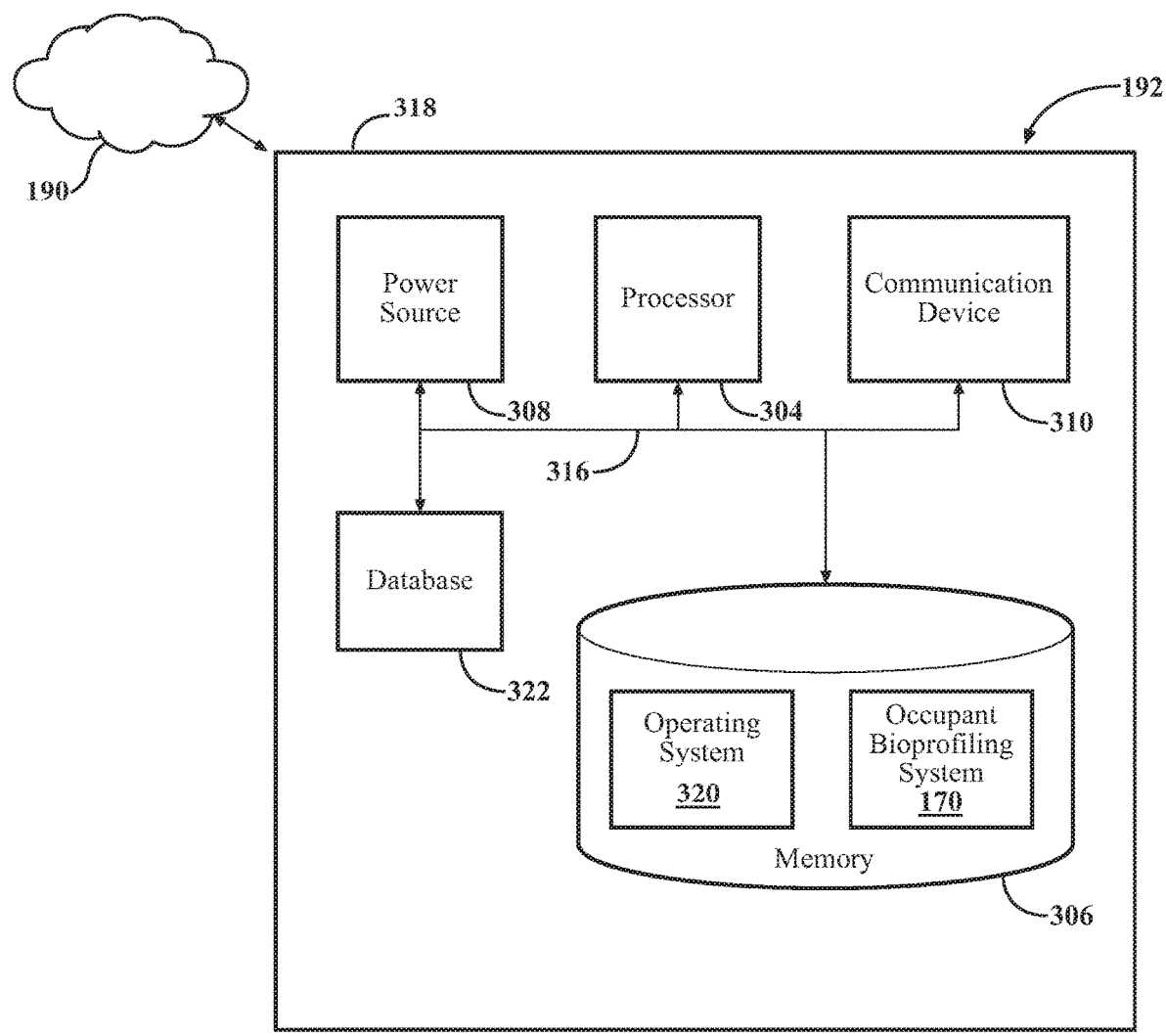
FIG. 3 is a block diagram of a computing device usable as part of the occupant bioprofiling system, according to embodiments described herein.

FIG. 3 is a block diagram of the computing device 192, as shown in FIG. 1, according to one or more embodiments. The computing device 192 can contain various components for performing the functions that are assigned to said server. The components can include a processor 304, like a central processing unit (CPU), a memory 306, a power source 308, communications device 310, input and/or output devices, and at least one bus 316 that connects the aforementioned components. In some embodiments, these components are at least partially housed within a housing 318.

The processor 304, which can also referred to as a CPU, can be a device which is capable of receiving and executing one or more instructions to perform a task as part of a computing device. In one embodiment, the processor 304 can include a microprocessor such as an application-specific instruction set processor, graphics processing unit (GPU), a physics processing unit (PPU), a DSP, an image processor, a co-processor, or others. Though referenced as the processor 304, it is understood that one or more processors 304 can be used in one or more embodiments described herein, including combinations of processors 304.

The memory 306 is any piece of hardware that is capable of storing data or information. Examples of data or information which can be stored in the memory 306 include, without limitation, data, program code in functional form, and/or other suitable information either on a temporary basis and/or a permanent basis. The memory 306 can include one or more modules that include computer-readable instructions that, when executed by the processor 304, cause the processor 304 to perform methods and functions that are discussed herein. The memory 306 can include volatile and/or non-volatile memory. The memory 306 can further include a computer-readable storage medium. Examples of suitable memory 306 include RAM, flash memory, ROM, EPROM, EEPROM (Electrically Erasable Programmable Read-Only Memory), registers, magnetic disks, optical disks, hard drives, or any other suitable storage medium, or any combination thereof.

The memory 306 can be a component of the processor(s) 304, or the memory 306 can be operably connected to the processor(s) 304 for use thereby. The memory 306 can include an operating system 320, such as LINUX. The operating system 320 can include batch, live, time sharing, real-time, and other types of operating systems. The operating system 320, as described herein, can include instructions for processing, accessing, writing, storing, searching data, or other functions as selected by the user for controlling and providing interface with the computing device 192. The memory 306 can include communications procedures for communicating with the network 190, computing devices, the vehicle 100, and/or another server.

The communication device 310 can be wired or wireless connection components and/or software allowing the computing device 192 to communicate with other computing devices. The communication device 310 can allow communication with devices either locally or remotely, such as over a network protocol (e.g., Ethernet or similar protocols). In one example, the computing device 192 is connected to the network 190 using the communication device 310. The communication device 310 can further be connected with remote devices associated with other computing devices. In one example, the communication device 310 is connected with the sensors system 120 and the data store 115 through the vehicle 100. In further embodiments, the computing device 192 can connect with one or more servers, allowing access to one or more sensors, which are connected to or in connection with the second server. The one or more sensors can include one or more of the sensors of the sensor system 120, described with reference to FIG. 1.

The computing device 192 can further include the occupant bioprofiling system 170 or components thereof. As described herein, certain components of the occupant bioprofiling system 170 can be stored in the vehicle 100, in the computing device 192 or in combinations thereof. As such, one or more embodiments of the occupant bioprofiling system 170 can include the occupant bioprofiling system 170, modules thereof, or components thereof as being stored, collected, created, compared or otherwise made available from the memory 306 or the database 322 of the computing device 192. When stored as part of the computing device 192, the occupant bioprofiling system 170 can access the vehicle 100, another computing device 192, one or more sensors, or other devices through the communications device 310 and the network 190, allowing for continuity between the one or more components which comprise the occupant bioprofiling system 170, as disclosed herein.

Figure 4:
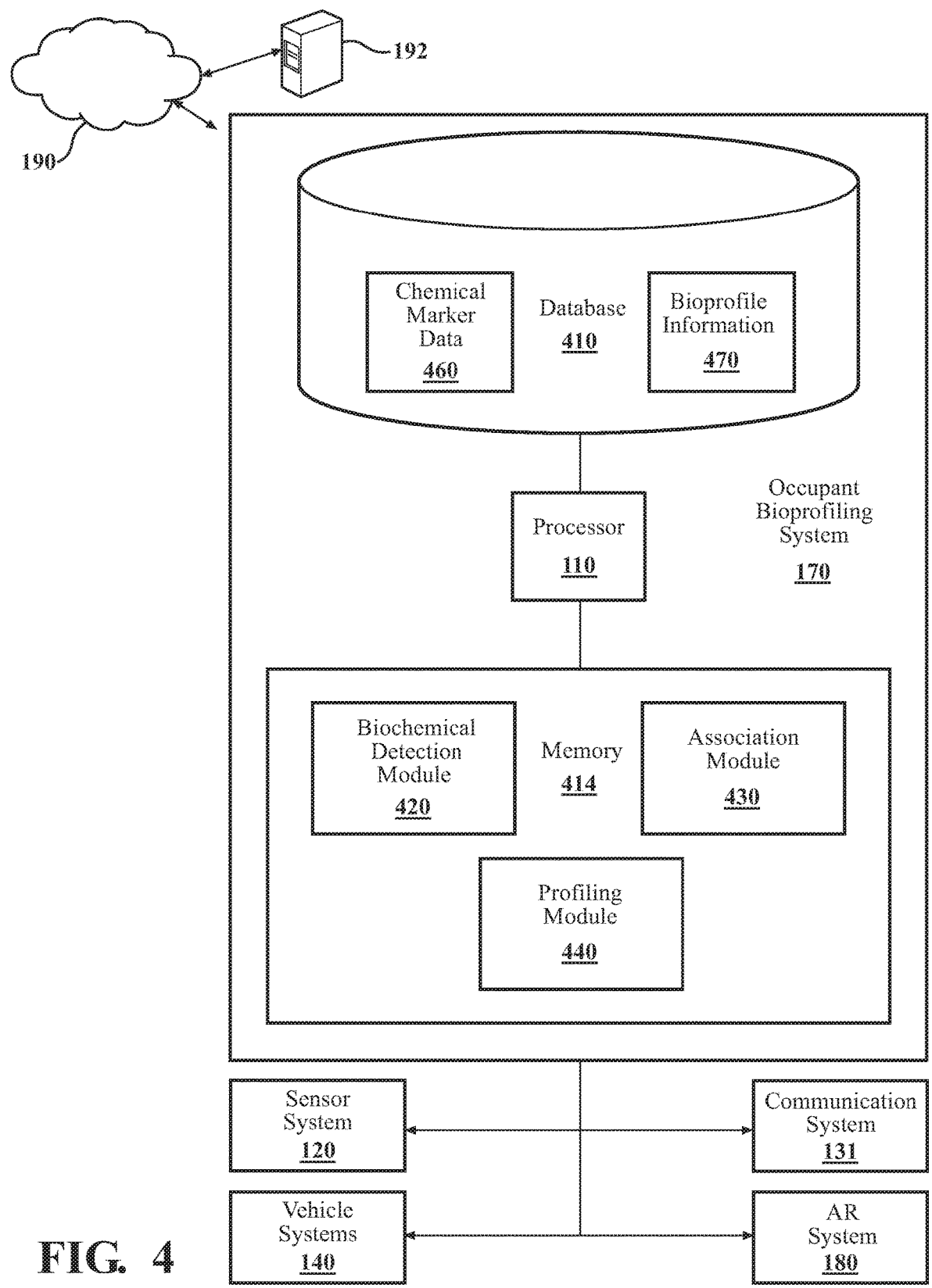
FIG. 4 is an illustration of the occupant bioprofiling system for vehicle positioning and benefit distribution in a vehicle platoon, according to embodiments described herein.

The discussion of the occupant bioprofiling system 170 begins at FIG. 4, with an illustration of the occupant bioprofiling system 170, according to one embodiment. The occupant bioprofiling system 170 is shown as including the processor 110 from the vehicle 100, depicted in FIG. 1. Accordingly, the processor 110 can be a part of the occupant bioprofiling system 170, the occupant bioprofiling system 170 can include a separate processor from the processor 110 or the occupant bioprofiling system 170 can access the processor 110 through a data bus or another communication path. In one embodiment, the occupant bioprofiling system 170 includes the memory 414 that stores a biochemical detection module 420, an association module 430 and a profiling module 440. The memory 414 is a RAM, ROM, a hard disk drive, a flash memory, or other suitable memory for storing the modules 420, 430, and 440. The modules 420, 430, and 440 are, for example, computer-readable instructions that when executed by the processor 110, cause the processor 110 to perform the various functions disclosed herein.

The occupant bioprofiling system 170 can further include a database 410. The database 410 can be presented in a number of configurations, including as part of the memory 414, as an independent component from the memory 414, as part of a separate memory (distinct from memory 414), or others. The database 410 can include chemical marker data 460 and bioprofile information 470. The chemical marker data 460 can include associations between diseases and chemistries, biochemical relations, pharmaceuticals (including prodrugs, degradation products and related chemistries), and other information which can be used to associate a chemical finding and a biological event. The chemical marker data 460 can include one or more data sets from remote sensors, as transmitted through a network 190 from a computing device 192, as well as data collected from one or more on vehicle sensors, such as from a sensor system 120. The bioprofile information 470 can include information related to detected occupants of the vehicle 100, including previous associations and tracking information. Though the occupant bioprofiling system 170 is shown as part of the vehicle 100, the occupant bioprofiling system 170 or portions thereof, can be stored in a separate vehicle, on a computing device, such as the computing device 192, or others. As such, one or more of the functions of the occupant bioprofiling system 170 or the modules contained therein, can be performed remotely and transferred to the collecting vehicle, such as the vehicle 100, as part of the embodiments described herein.

The occupant bioprofiling system 170 can generally begin with the biochemical detection module 420. The biochemical detection module 420 can generally include instructions that function to control the processor 110 to detect one or more enclosure-related chemicals, the enclosure-related chemicals including biochemicals expelled by one or more occupants. The environment of the interior of the vehicle can include chemicals expelled by the one or more occupants, outgassed from one or more materials in the vehicle 100, drawn in through the air handling system from the exterior, or others which compose the interior gases of the vehicle. Expelled includes any kind of release from the occupants including secretions, excretions, exhalations, or others which provide biochemical data. Enclosure-related chemicals are biologically-related organic and inorganic chemicals which are available to the interior of the vehicle 100. Enclosure-related chemicals can include chemicals produced by, having a direct effect on, or expelled from any organism in the vehicle 100. The enclosure-related chemicals can include expelled liquids or gases internalized and/or externalized by human or animal occupants, bacteria, or other organisms within or in communication with the interior of the vehicle 100.

The biochemical detection module 420 can include instructions to access a chemical detection device, such as the chemical detection device 127. In one embodiment, the biochemical detection module 420 can include instructions to determine detectable markers about the enclosure-related chemicals from the interior of the vehicle 100. The biochemical detection module 420 can cause the chemical detection device 127 to collect samples at numerous intervals, such as continuous, intermittent, random, time-framed or others. The enclosure-related chemicals included in the samples from the interior of the vehicle 100 can include detectable markers. Detectable markers are chemical components, temporal information, correlations between chemicals or other factors which can be applied to differentiate the source of the chemical. In one example, the detection of acetone (which can be used as an indicator of ketosis) in one occupant can distinguish that occupant from another occupant which does not produce acetone. In another example, the detection of isoprene (a degradation product of dimethylallyl pyrophosphate and an indicator of high cholesterol) in one occupant can distinguish from another occupant who produces isoprene in significantly lower quantities or alongside other markers. Thus, the biochemical detection module 420 can produce a variety of information regarding temporal parameters, locations of detection, possible chemical markers, or other source indicia for the detectable markers. The chemical constituents, including detectable markers, as determined through the chemical detection device and the occupant bioprofiling system 170, can be stored as part of the bioprofile information 470 in the database 410.

Related to detectable markers, the chemical marker data 460 can further include profile signatures related to various disease states. Profile signatures are determined chemicals and chemical concentrations that can serve as a profile for one disease as differentiated from another. The profile signatures can be a combination of detectable markers which vary as a function of time, activity, location, or other which are diagnostic when considered together. Using the first example from above, the detection of acetone (which can be used as an indicator of ketosis) can be part of a profile signature for Type I or Type II diabetes mellitus. In another example, the detection of isoprene (a degradation product of dimethylallyl pyrophosphate and an indicator of high cholesterol) can be part of a profile signature for hypertension or hypercholesterolemia. Thus, the detectable markers serve to connect chemicals to individuals, while profile signatures connect chemicals to diseases or other biological events.

The association module 430 can generally include instructions that function to control the processor 110 to associate one or more of the enclosure-related chemicals to an associated occupant of the one or more occupants. The above described detectable markers, as detected through the biochemical detection module 420, can be employed to determine a variety of associations, such as which occupant is the source of which chemistry or which sample. Associations created by the association module 430 can include event associations and occupant associations. Event associations are associations formed between a specific chemical or concentration (e.g., the profile signatures) and a specific event, such as disease, toxicity, or others. Occupant associations are associations of chemicals to a specific occupant (e.g., the detectable markers). The chemistries can be associated with an event or an occupant independent of one another. Timing, location, rate of availability (indicating respiration rate), or other factors can be incorporated through artificial intelligence to determine chemical patterns distinct between occupants, thus creating a profile signatures from one or more detectable markers. The association module 430 can compare the profile signatures and the detectable markers to the chemical marker data 460 to determine possible event associations. Possible event associations can include disease states, toxicology profiles, infections, or other detectable markers and patterns. All possible associations can then be recorded in the bioprofile information 470 of the database 410.

In further embodiments, one or more of the enclosure-related chemicals can be associated with an occupant in the absence of a specific state (i.e., homeostatic associations). Without intending to be bound by theory, it is understood that the combinations of various homeostatic parameters in the human body can provide indications of changes in the person. Said changes, reflected in expelled chemistry from the occupant are homeostatic associations. These changes can be positive, negative or innocuous. In one or more embodiments, the association module 430 can monitor for changes reflecting homeostatic changes in the occupant through the enclosure-related chemicals to determine heuristically if an issue, event, or complication is related to one or more homeostatic changes. In one example, the association module 430 determines over a period of time that chemical Z is related to a first occupant and concentrations produced are appearing to increase over time (including possible detectable markers for the chemical). The first occupant has an adverse event and is rushed to a hospital from the vehicle 100. The association module 430 can then create a homeostatic association (including a possible profile signature for the chemical), such as marking the event and chemical Z to watch for similar events in other occupants, providing this association to a medical professional for further evaluation, associating chemical Z to the adverse event or others. The event associations and the homeostatic associations can further include occupant associations as they are determined. The associations, the chemicals, the adverse event and any related information can be stored by the association module 430 in the chemical marker data 460 in the database 410.

The profiling module 440 can generally include instructions that function to control the processor 110 to create a biological profile for an associated occupant. The biological profile is a temporal and holistic collection of associations, as they relate to a specific occupant. As such, the biological profile can include medical information and historical information related to the enclosure-related chemicals. The profiling module 440 can receive the associations produced by the association module 430 and can make one or more determinations regarding the associated occupant. The determinations can include eminent changes in disease state, possible clinical indications for the occupant, required or advisable restrictions for the occupant (e.g., possible incapacitation due to illness, detected drug use, intoxication, etc.), or others. The determinations can be stored in the bioprofile information 470, as part of biological profile for the associated occupant. The biological profile can be specific to the associated occupant. Further, the biological profile can be collected over time, across multiple platforms or sources. In further embodiments, the biological profile can include logical determinations between chemical detections and/or detectable markers and clinical indications as provided by secondary sources, such as a medical doctor or other clinician.

The profiling module 440 can further include instructions to screen out one or more infiltrating chemicals. The profiling module 440, in determining the biological profile of the occupant, can further determine that one or more biochemicals are coming from non-occupant sources. Mold growth, decaying matter (e.g., left-over food in the vehicle), or others can be a source of biochemicals which are not associated with the occupants. Thus, the profiling module 440 can filter out results from said biochemicals as background noise. In further embodiments, the biological profile can include statistical analysis regarding changes in concentrations. Said statistical analysis can allow for connections between disparate events, leading to exclusion or inclusion of detected chemicals in the biological profiles.

In further embodiments, the profiling module 440 can include genetic information. Genetic information can be gathered from a variety of sources, such as saliva, skin, blood or others. In one embodiment, the profiling module includes a genetic material sampler. The genetic material sampler can be substantially similar to the genetic material sampler 270, described with reference to FIG. 2. The genetic information can be received from a secondary source, such as a genetic analysis performed through a third party. The genetic information can provide an indication as to the source of the chemicals detected by the chemical detection device. In further instances, the chemicals detected by the occupant bioprofiling system 170 can be treated as a phenotype and compared to one or more genotypes in determinations of biological events for the occupant.

In further embodiments, the profiling module 440 can include physical parameters of the occupant in the biological profile through one or more physiological detection devices. The physiological detection devices can include blood pressure monitors, heart monitors, NIRS devices, weight scales and others. In this embodiment, the biological profile can include blood pressure, pulse, weight, gender, cardiovascular response, medications (including related adverse events and physiological changes), and others. As such, specific chemistries can be associated to the physiology of the occupant for better diagnosis or determination of medical issues or related homeostatic changes. In one example, the occupant can be in contact with a blood pressure monitoring device, capable of determining systolic/diastolic pressures, blood oxygenation, and pulse rate. Further, the vehicle 100 can be equipped with occupant bioprofiling system 170 and a chemical detection device 127 as described above. As such, the vehicle collects information regarding physiological parameters of the cardiovascular system and chemistries, as expelled from the occupant. In this example, the occupant produces a first chemical known to be related to a number of lung diseases, including lung cancer and pulmonary edema. The occupant bioprofiling system 170 can also detect low oxygenation of the blood, heightened systolic and diastolic pressures, and heightened pulse using the physiological detection devices. Thus, the vehicle 100, through the occupant bioprofiling system 170, can determine a higher likelihood of pulmonary edema concomitant with possible congestive heart failure over lung cancer.

In further embodiments, the occupant bioprofiling system 170 can further apply the occupant-specific biological profile in data analytics. The collected biological profiles and other information of a plurality of occupants can be accumulated in a computing device, such as a server or other computing device. The data collected from the occupants can then be applied and analyzed to determine connecting factors between the data, such as through an artificial intelligence (AI) and/or big data mechanism. Artificial intelligence focuses on problem solving with human-like ability to create and define associations. Artificial intelligence approaches can include evolutionary schemes, such as genetic algorithms; Nouvelle AI; neural networks; probabilistic methods, such as a Bayesian network or hidden Markov models; or others. Big data analyzes extremely large data sets to create associations and determinations about the data. Big data and artificial intelligence can be applied in conjunction. Thus, the data collected can be analyzed for associations between occupants, between disease states, between chemicals and diseases (e.g., to exclude false positive and negatives), to determine currently unknown medical conditions or disease states, or others. The resulting associations can be applied to update the occupant bioprofiling system 170 or components thereof, updating a database of correlated biomarkers, or others, as desired.

Figure 5:
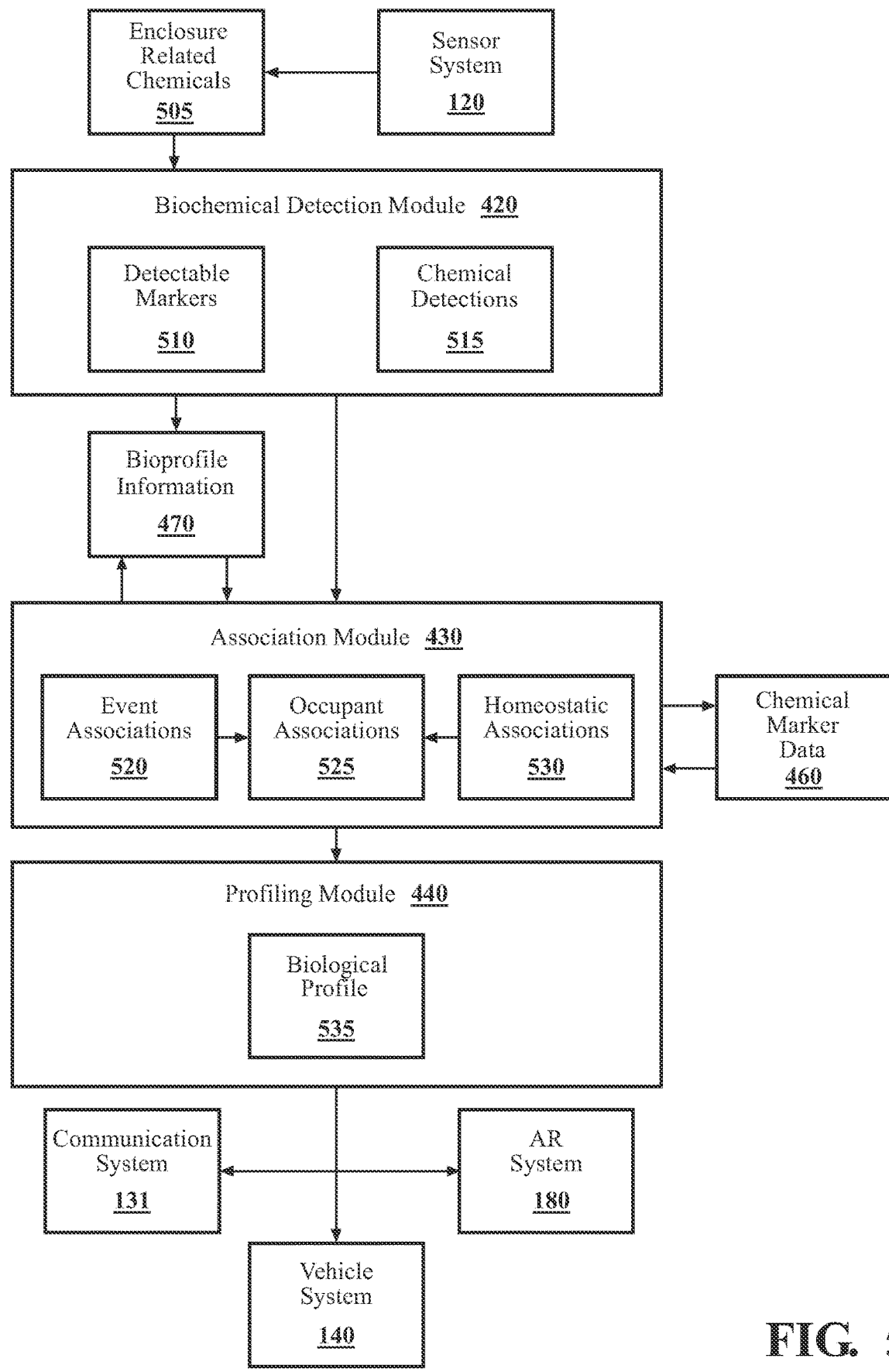
FIG. 5 is a schematic of the occupant bioprofiling system, according to one or more embodiments.

FIG. 5 depicts a schematic 500 of the occupant bioprofiling system 170, according to one or more embodiments. The occupant bioprofiling system 170 collects chemical data about the interior of the vehicle 100, using the chemical detection device 127. The chemical data, which includes enclosure-related chemicals from the occupants, is then associated to the one or more occupants as part of the bioprofile information 470 and connected with chemical marker data 460 to create the biological profile and make other determinations. Thus, the occupant bioprofiling system 170 can provide information about the occupants, as collected from available chemistry over time in the vehicle 100.

The schematic 500 begins with the biochemical detection module 420 receiving data on enclosure-related chemicals 505. The enclosure-related chemicals can be detected by the sensor system 120, described with reference to FIGS. 1-3. The biochemical detection module 420 can determine detectable markers 510 from the data regarding the enclosure-related chemicals 505. The detectable markers 510, in embodiments described herein, are chemical, temporal, or relational indications of the source of the chemical. The biochemical detection module 420 can further determine chemical detections 515 from the data for the enclosure-related chemicals. The chemical detections 515 are the various molecules which are available in the enclosure-related chemicals 505. The chemical detections 515 can include types of chemicals, as well as quantities, timing and other available data related to the specific chemicals in the sample.

The biochemical detection module 420 can then forward the detectable markers 510 and the chemical detections 515 to the bioprofile information 470 and to the association module 430. The association module 430 can include instructions to create event associations 520, occupant associations 525, and homeostatic associations 530. The event associations can be determined using the chemical marker data 460. The chemical marker data 460 can include one or more indications regarding events, as associated to chemical information. The chemical information from the chemical detections 515 can be applied to the information available from the chemical marker data 460 to make one or more event associations 520. The association module 430 can further apply the detectable markers 510 to determine one or more occupant associations 525. The homeostatic associations 530 can include data from the detectable markers 510 and the chemical detections 515. Once the homeostatic associations 530 and the event associations are determined, these associations can be further associated to the occupant (i.e., occupant associations 525). The event associations 520, the occupant associations 525, and the homeostatic associations 530 can then be incorporated into the bioprofile information 470. Further, the chemical marker data 460 can be modified using the above associations, such as the homeostatic associations 530.

The event associations 520, the occupant associations 525, and the homeostatic associations 530 can further be forwarded to the profiling module 440 for incorporation into the biological profile 535. The profiling module 440 can include instructions to create the biological profile for the one or more occupants. The biological profile can include medical information, physiological information, toxicology information and others as derived from the event associations 520, the occupant associations 525, and homeostatic associations 530. The profiling module 440 can present or otherwise make the biological profile 535 available to the occupant or others as desired. In one embodiment, the biological profile 535 can include a graphical analysis of the chemicals present, including type and quantity, various medical conditions which are believed to be related to said chemicals, indications of illicit drug use or alcoholism, or others. The biological profile 535 can present this information to the occupant using the communications system 131 and/or the AR system 180. Further, the biological profile 535 can provide indications that the occupant is not fit for operation of the vehicle, such as due to alcohol use or acute disease state. As such, the profiling module 440 can disable the vehicle 100 or put the vehicle 100 in an autonomous state to protect the occupants or others.

In one or more embodiments, the occupant bioprofiling system 170, or components thereof, can be portable. The occupant bioprofiling system 170, or the one or more components thereof can be stored on a remote computing device from the vehicle 100. The remote computing device can be substantially similar to the computing device 192, described with reference to FIG. 3. Specific examples of the remote computing device, usable with embodiments described herein, can include servers, embedded systems, smart phones, personal computers, or other devices capable of storing, processing, and/or transmitting the above described data. Through the use of the remote computing device, the occupant bioprofiling system 170, or the one or more components thereof, can be available to the occupant, third parties, a secondary vehicle incorporating the occupant bioprofiling system 170, or others, which are remote from the vehicle 100.

In an exemplary embodiment, the occupant can provide information to the occupant bioprofiling system 170 in the vehicle 100. As described above, the occupant bioprofiling system 170 collects information related to the one or more occupants (e.g., the biochemical profile) using the biochemical detection module 420, the association module 430, the profiling module 440, the chemical marker data 460 and the bioprofile information 470. Said information can then be stored locally and/or remotely in a database, such as the database 410. The biological profile 535, the chemical marker data 460, and the bioprofile information 470 can thus be made available via the network 190 to other parties. The biological profile 535, the chemical marker data 460, and the bioprofile information 470 can be applied in a variety of ways, such as to update a remote implementation of the occupant bioprofiling system 170, regarding occupant specific information (e.g., when buying a new vehicle or riding in a friend's vehicle).

The occupant bioprofiling system 170 can thus provide numerous benefits to the occupant. The occupant bioprofiling system 170 can determine a health state for the occupant, thus guiding care for the occupant prior to medical need. The occupant bioprofiling system 170 can provide information specific to the occupant to clinicians to help determine the source of illness. The occupant bioprofiling system 170 can detect imminent incapacitation thus helping an occupant avoid an accident or properly begin autonomous control. Further, the occupant bioprofiling system 170 can make clinical associations to specific chemistries in a heuristic manner.

Figure 6:
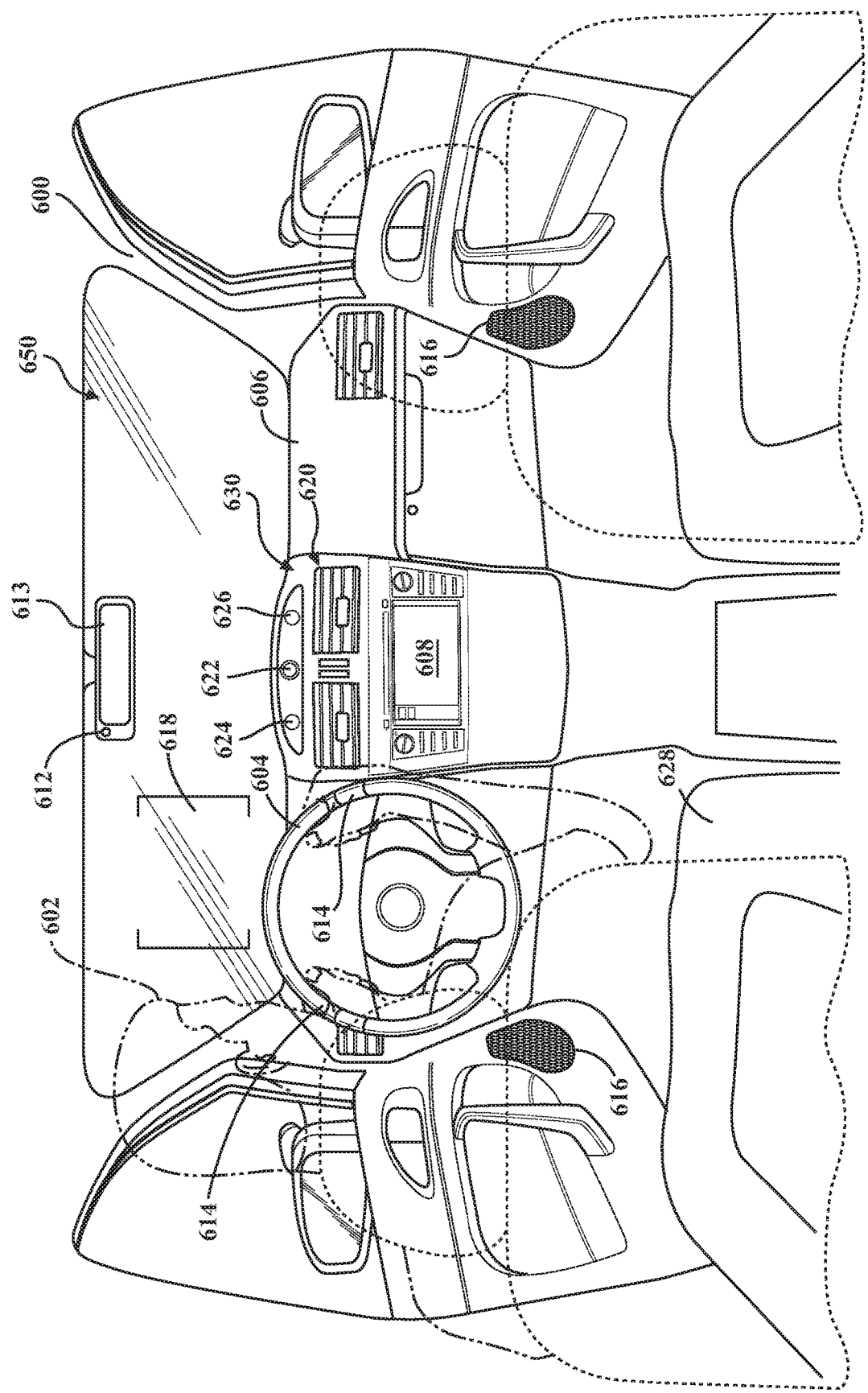
FIG. 6 is an illustration of a bioprofiling vehicle, according to one or more embodiments.

FIG. 6 depicts an exemplary interior 600 for the vehicle 100. The interior 600, also referred to in some embodiments as the passenger compartment, can include a variety of vehicle-appropriate components, including a steering wheel 604, and a dashboard 606. As shown here, the interior 600 of the vehicle 100 can include an air handling system 620, which receives and circulated the air within the interior 600. The air handling system 620 is shown here as including a set of vents, a first collection port 622, a second collection port 624, and a third collection port 626. The air handling system 620 can be in fluid communication with the chemical detection device 127. The interior 600 can further include the communication system 131, depicted here as including displays, a microphone 610, and one or more speakers 616. The displays can be in a variety of forms, such as a screen display 608 shown as part of a console 630, an augmented reality display 618 shown as part of the windshield 650, other displays, or combinations thereof.

The interior 600 can further include one or more physiological detection devices. The one or more physiological detection devices can be any device capable of and configured to collect biometric data and/or biological samples from the one or more occupants. Biometric data can include blood pressure, pulse, body fat percentages, blood oxygenation, and others. As described above, biological samples can include biological components captured from the one or more occupants such as lost hair, excreted sweat (e.g., from hands of an occupant 602 on a steering wheel 604), cell samples (e.g., as collected by the genetic material sampler 270), or others. Shown here, the physiological detection devices include an image capture device 612 and a biometric collection device 614. The biometric collection device 614, shown here positioned on the steering wheel 604, can collect blood pressure, blood oxygenation, pulse rate and/or other details relevant to occupant physiology. The image capture device 612, shown here positioned in the mirror 613, can detect facial changes which can indicate alertness and awareness, respiration rates, body temperature (such as in the case of IR cameras), and other visible health parameters.

In further embodiments, the biometric collection device 614 can receive and collect biological samples from the occupant 602, such as sweat and oils, as externalized from the occupant 602. The biological samples can then be channeled to the chemical detection device 127 or stored for further analysis. In another embodiment, the biometric collection device 614 can be positioned in or work in conjunction with other components of the interior, such as the seat 628, for collection of biological samples or physiologically relevant information. In yet further embodiments, the seat 628 can be a separate physiological detection device, working independent of the biometric collection device 614. As such, the seat 628 can include one or more microchannels (not shown) for collection of said biological samples.

The occupant bioprofiling system 170 can begin with instructions from biochemical detection module 420, detecting the presence of one or more occupants and beginning the collection of the samples for detection of the enclosure-related chemicals. In this example, the biochemical detection module 420 collects samples through a first collection port 622 of the air handling system 620. In this embodiment, the samples are then directed to the chemical detection device 127 for determination of the chemical components of the sample. In further embodiments, the chemical detection device 127 can be composed of a plurality of devices, receiving the samples through the first collection port 622 and dividing the sample between multiple component devices, either in series or in parallel. In another embodiment, the chemical detection device 127 can be composed of a plurality of devices, receiving the samples through the first collection port 622, the second collection port 624 and the third collection port 626. The samples can be dividing between multiple devices or delivered in whole to individual component devices of the chemical detection device 127, either in series or in parallel.

In this example, an occupant 602 is positioned in the driver seat with his hands on the steering wheel 604 and in contact with the biometric collection device 614. The occupant 602 is driving the vehicle 100 and performing standard bodily functions, such as metabolism and respiration (breathing). As the occupant 602 breathes, he is expelling various chemicals related to the biological processes going on in his body. The biochemical detection module 420 sends instructions to cause the chemical detection device 127 to collect a sample from the first collection port 622, the second collection port 624 and the third collection port 626. The sample includes enclosure-related chemicals, such as expelled gases and liquids from the occupant 602 and ambient gases from the interior of the vehicle 100. The chemical detection device 127 determines the available chemicals in the sample, including organic and inorganic chemicals from the vehicle 100 and the occupant 602. The biochemical detection module 420 can add information to the bioprofile information related to the chemicals detected, including available information regarding detectable markers of the chemicals. The bioprofile information and the detections can then be transferred to the association module 430.

The association module 430 can then provide instructions to associate one or more of the enclosure-related chemicals to an associated occupant. The association module 430 can compare the detected chemicals to the chemical marker data 460, to create one or more associations. The association module 430 can then produce event associations (e.g., a chemical was produced which is related to emphysema), occupant associations (e.g., occupant 602 produced thirteen (13) chemicals detectable in the sample), and homeostatic associations (e.g., one of the chemicals is inorganic and appears only when the occupant 602 has labored breathing, however the connection of said chemical to the event is unknown). Said associations can then be added to the bioprofile information 470 as well as to update the chemical marker data 460.

The enclosure-related chemicals can include one or more detectable markers which indicate the source of the chemicals. The detectable markers could be known origin (e.g., a biochemical only produced by humans), related to known conditions (e.g., the owner of the vehicle is known to have high blood pressure and the chemical is related to high blood pressure), related to physiological parameters (e.g., the occupant 602 has a respiration rate of 18 breathes per minute and this matches the rhythm of the detections), or others. In this example, a detectable chemical signature can be used to determine if chemicals are produced by the occupant 602, such as combinations of chemicals that are present when the occupant 602 produces a specific chemical, indicating the likelihood that the chemistry was produced by the occupant 602.

In further embodiments, the collection ports 622, 624 and 626 can be used to triangulate a general location of the source of the chemistry. Without intending to be bound by theory, it is believed that as chemicals are produced, they will move at a constant rate from their source, based on fluid dynamics of the environment. As such, detection of a specific chemistry is expected to occur faster at ports closer to the source. This information can be used, alongside the specific chemistries detected to associate said chemistries to an occupant, such as occupant 602. As shown here, the occupant 602 is detected at the collection port 624 before the collection port 622 and the collection port 626. This gives an indication to the association module 430 that the occupant source of the chemistry is the occupant 602.

The profiling module 440 can then provide instructions to create a biological profile for the associated occupant. In this example, the profiling module 440 collects the chemical information and the associations from the association module 430 and determines that the occupant 602 has developed signs of pre-clinical emphysema. Further, the profiling module 440 notes that an inorganic chemical is present when breathing is difficult, indicating that the chemical may be an irritant for the condition or possibly causative. The occupant bioprofiling system 170 can include a level of correlation, and a variety of other details to assist a clinician in diagnosing illness and treatment. This information can be presented to the occupant 602 through the communications system 131 and/or the AR system 180. The AR system 180 can control the augmented reality display 618 whereas the communications system 131 can control the screen display 608. The display can include medical information, guidance on going to a doctor, specific parameters detected, and other optional resources and choices for the occupant 602.

Thus, the occupant bioprofiling system 170 provides numerous benefits to the occupant 602. The occupant bioprofiling system 170 detects biological changes to the occupant 602, thus allowing for early response and treatment of detected illness or disease. Further, the occupant bioprofiling system 170 can determine connections of specific unknown chemicals to adverse events in the occupant 602. Further, the occupant bioprofiling system 170 can create a biological profile of the occupant 602 such that data can be extracted over time, adding to knowledge about occupant 602 and medical knowledge generally.

Figure 7:
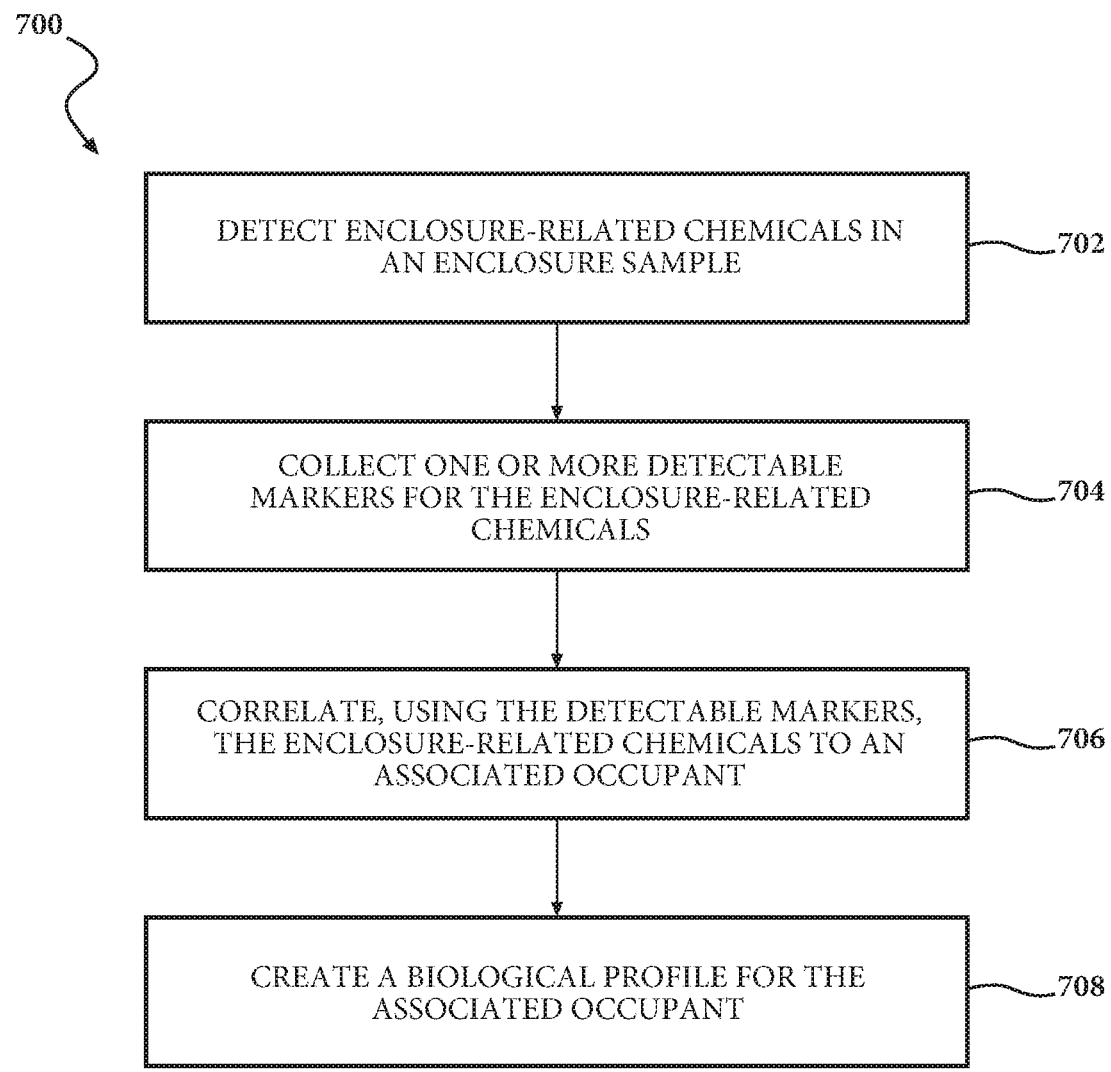
FIG. 7 is a block diagram of a method for determining biological aspects of occupants, according to one or more embodiments.

FIG. 7 is a block diagram of a method 700 for determining biological aspects of occupants, according to one or more embodiments herein. The method 700 detects enclosure-related chemicals in the vehicle. Using known and unknown associations, the method 700 then determines the relationship of the chemicals to events and occupants. Then, using the above described associations, the method 700 creates or modifies a biological profile for each of the occupants, thus indicating medical, toxicological or historical information related to expelled chemistries in the vehicle. The method 700 can begin with detecting enclosure-related chemicals, at 702. One or more detectable markers can be collected for one or more of the enclosure-related chemicals, at 704. One or more of the enclosure-related chemicals can then be associated to an associated occupant of the one or more occupants, at 706. Then, a biological profile can be created for the associated occupant, at 708.

The method 700 can begin with detecting enclosure-related chemicals, at 702. The enclosure-related chemicals can include chemicals expelled by one or more occupants. The environment of the interior of the vehicle can include chemicals expelled by the one or more occupants, outgassed from one or more materials in the vehicle, drawn in through the air handling system from the exterior, or others which compose the interior gases of the vehicle. Expelled includes any kind of release from the occupants including secretions, excretions, exhalations, or others which provide biochemical data. Enclosure-related chemicals are biologically-related organic and inorganic chemicals which are available to the interior of the vehicle. Enclosure-related chemicals can include chemicals produced by, having a direct effect on, or expelled from any organism in the vehicle. The enclosure-related chemicals can include expelled liquids or gases internalized and/or externalized by human or animal occupants, bacteria, or other organisms within or in communication with the interior of the vehicle.

The detection of enclosure-related chemicals can be performed as part of a system, such as the occupant bioprofiling system 170, described with reference to FIGS. 1 and 4. The occupant bioprofiling system 170 can include the biochemical detection module 420. The biochemical detection module 420 can generally include instructions that function to control the processor 110 to detect one or more enclosure-related chemicals, the enclosure-related chemicals including biochemicals expelled by one or more occupants. The enclosure-related chemicals and the chemical detection device can be substantially similar to the enclosure-related chemicals and the chemical detection device 127, described with reference to FIGS. 1-3. The enclosure-related chemicals can be detected in a substantially similar fashion to the enclosure-related chemicals, described with reference to FIGS. 1-3. The biochemical detection module 420, to detect chemicals in the sample, can access the chemical detection device 127 of the vehicle 100, described with reference to FIGS. 1 and 2. The detected chemicals of the enclosure-related chemicals can be stored as part of the bioprofile information 470. The bioprofile information 470 can be stored in a database, such as the database 410, described with reference to FIG. 4.

One or more detectable markers can be collected for one or more of the enclosure-related chemicals, at 704. The method 700 can include accessing a chemical detection device, such as the chemical detection device 127. The chemical detection device can then collect detectable markers for the enclosure-related chemicals within the samples from the interior of the vehicle 100. The method 700 can include causing the chemical detection device 127 to collect samples at numerous intervals, such as continuous, intermittent, random, time-framed or others. The samples from the interior of the vehicle 100 can include detectable markers. Detectable markers are indicia which can be used to differentiate the source of the chemical components from the sample. The detectable markers can be substantially similar to the detectable markers described with reference to FIG. 4. A detectable marker or a series or detectable markers can be employed in the embodiments described herein to differentiate between occupants or other sources.

The collection of detectable markers can be performed as part of a system, such as the occupant bioprofiling system 170, described with reference to FIGS. 1 and 4. The occupant bioprofiling system 170 can include the biochemical detection module 420. The biochemical detection module 420 can generally include instructions that function to control the processor 110 to collect one or more detectable markers for one or more of the enclosure-related chemicals. The detectable markers can be substantially similar to the detectable markers, described with reference to FIG. 4. The detectable markers can be detected in a substantially similar fashion to the detectable markers, described with reference to FIG. 4. The biochemical detection module 420, to collect said detectable markers in the sample, can access the chemical detection device 127 of the vehicle 100, described with reference to FIGS. 1 and 2. The detectable markers can be stored as part of the bioprofile information 470. The bioprofile information 470 can be stored in a database, such as the database 410, described with reference to FIG. 4.

The one or more of the enclosure-related chemicals can be associated to an associated occupant of the one or more occupants, using the detectable markers, at 706. The above described detectable markers, as detected through the method 700, can be employed to determine which occupant is the source of which chemistry or which sample. Timing, location, rate of availability (indicating respiration rate), or other factors can be incorporated through artificial intelligence to determine chemical patterns distinct between occupants, thus creating a profile signature from one or more detectable markers. The method 700 can compare the collected chemistries and the detectable markers to determine possible associations. Possible associations can include event associations, such as disease states, toxicology profiles, infections, or other detectable markers and patterns. In another embodiment, the possible associations can include occupant associations. In further embodiments, one or more of the enclosure-related chemicals can be associated with an occupant in the absence of a specific state (i.e., homeostatic associations). In one or more embodiments, the method 700 can monitor for changes reflecting homeostatic changes in the occupant through the enclosure-related chemicals to determine heuristically if an issue, event, or complication is related to one or more homeostatic changes. The event associations and the homeostatic associations can further include occupant associations as they are determined.

The association of enclosure-related chemicals to events and occupants can be performed as part of a system, such as the occupant bioprofiling system 170, described with reference to FIGS. 1 and 4. The occupant bioprofiling system 170 can include the association module 430. The association module 430 can generally include instructions that function to control the processor 110 to associate one or more of the enclosure-related chemicals to the associated occupant of the one or more occupants. The enclosure-related chemicals can be substantially similar to the enclosure-related chemicals, described with reference to FIGS. 1-3. The enclosure-related chemicals can be compared to known chemical associations in a substantially similar fashion to the enclosure-related chemicals, described with reference to FIGS. 1-3. The association module 430 can reference the chemical marker data 460 and create event associations, occupant associations and homeostatic associations, as described with reference to FIGS. 1 and 2. The associations can be stored as part of the bioprofile information 470. Homeostatic associations can be applied to the chemical marker data 460, such as to update available data or to create additional associations. The chemical marker data 460 and the bioprofile information 470 can be stored in a database, such as the database 410, described with reference to FIG. 4.

Then, a biological profile can be created for the associated occupant, at 708. The biological profile can include medical information and historical information related to the enclosure-related chemicals. The biological profile is a temporal and holistic collection of associations, as they relate to a specific occupant. As such, the biological profile can include medical information and historical information related to the enclosure-related chemicals. The method 700, using the associations produced previously, can make one or more determinations regarding the occupant. The determinations can include eminent changes in disease state, possible clinical indications for the occupant, required or advisable restrictions for the occupant (e.g., possible incapacitation due to illness, detected drug use, intoxication, etc.), or others. The biological profile can be specific to the occupant. Further, the biological profile can be collected over time, across multiple platforms or sources. In further embodiments, the biological profile can include logical determinations between chemical detections and/or detectable markers and clinical indications as provided by secondary sources, such as a medical doctor.

The method 700 can further include instructions to screen out one or more infiltrating chemicals. The method 700, in determining the biological profile of the occupant, can further determine that one or more biochemicals are coming from non-occupant sources. Thus, the method 700 can filter out results from mold growth, decaying matter, or others as background noise. In further embodiments, the biological profile can include statistical analysis regarding changes in concentrations. Said statistical analysis can allow for connections between disparate events, leading to exclusion or inclusion of detected chemicals in the biological profiles.

In further embodiments, the profiling module 440 can include genetic information. Genetic information can be gathered from a variety of sources, such as saliva, skin, blood or others. The genetic information can be received from a secondary source, such as a genetic analysis performed through a third party. The genetic information can provide an indication as to the source of the chemicals detected by the chemical detection device. In further instances, the chemicals detected by the method 700 can be treated as a phenotype and compared to one or more genotypes from the genetic information in determinations of biological events for the occupant.

In further embodiments, the method 700 can include physical parameters of the occupant in the biological profile through one or more physiological detection devices. The physiological detection devices can include blood pressure monitors, heart monitors, NIRS devices, weight scales and others. In this embodiment, the biological profile can include blood pressure, pulse, weight, gender, cardiovascular response, medications (including related adverse events and physiological changes), and others. As such, specific chemistries can be associated to the physiology of the occupant for better diagnosis or determination of medical issues or related homeostatic changes. In one example, the occupant can be in contact with a blood pressure monitoring device, capable of determining systolic/diastolic pressures, blood oxygenation, and pulse rate.

The biological profile can be created for the associated occupant as part of a system, such as the occupant bioprofiling system 170, described with reference to FIGS. 1 and 4. The occupant bioprofiling system 170 can include the profiling module 440. The profiling module 440 can include instructions that function to control the processor 110 to create a biological profile for an associated occupant. The biological profile can be substantially similar to the biological profile, described with reference to FIGS. 1-3. The biological profile can includes event, occupant and homeostatic associations in a substantially similar fashion to the biological profile, described with reference to FIGS. 1-3. The profiling module 440 can further provide determinations regarding health, condition, or other known factors, as described with reference to FIG. 1-4. The biological profile can be stored as part of the bioprofile information 470. The bioprofile information 470 can be stored in a database, such as the database 410, described with reference to FIG. 4.

Thus, the method 700 provides numerous benefits to the associated occupant. The method 700 detects biological changes to the associated occupant, thus allowing for early response and treatment of detected illness or disease. Further, the method 700 can determine connections of specific unknown chemicals to adverse events in the associated occupant. Further, the method 700 can create a biological profile of the associated occupant such that data can be extracted over time, adding to knowledge about associated occupant and medical knowledge generally.

Detailed embodiments are disclosed herein. However, it is to be understood that the disclosed embodiments are intended only as examples. Therefore, specific structural and functional details disclosed herein are not to be interpreted as limiting, but merely as a basis for the claims and as a representative basis for teaching one skilled in the art to variously employ the aspects herein in virtually any appropriately detailed structure. Further, the terms and phrases used herein are not intended to be limiting but rather to provide an understandable description of possible implementations. Various embodiments are shown in FIGS. 1-7, but the embodiments are not limited to the illustrated structure or application.

The flowcharts and block diagrams in the figures illustrate the architecture, functionality, and operation of possible embodiments of systems, methods and computer program products according to various embodiments. In this regard, each block in the flowcharts or block diagrams can represent a module, segment, or portion of code, which can include one or more executable instructions for implementing the specified logical function(s). It should also be noted that, in some alternative embodiments, the functions noted in the block can occur out of the order noted in the figures. For example, two blocks shown in succession can, in fact, be executed substantially concurrently, or the blocks can sometimes be executed in the reverse order, depending upon the functionality involved.

The systems, components and/or methods described above can be realized in hardware or a combination of hardware and software and can be realized in a centralized fashion in one processing system or in a distributed fashion where different elements are spread across several interconnected processing systems. Any kind of processing system or other apparatus adapted for carrying out the methods described herein is suited. A typical combination of hardware and software can be a processing system with computer-usable program code that, when being loaded and executed, controls the processing system such that it carries out the methods described herein. The systems, components and/or methods also can be embedded in a computer-readable storage, such as a computer program product or other data programs storage device, readable by a machine, tangibly embodying a program of instructions executable by the machine to perform methods and methods described herein. These elements also can be embedded in an application product which can include all the features enabling the embodiment of the methods described herein and, which when loaded in a processing system, is able to carry out these methods.

Furthermore, embodiments described herein can take the form of a computer program product embodied in one or more computer-readable media having computer-readable program code embodied or embedded, such as stored thereon. Any combination of one or more computer-readable media can be utilized. The computer-readable medium can be a computer-readable signal medium or a computer-readable storage medium. The phrase "computer-readable storage medium" means a non-transitory storage medium. A computer-readable storage medium can be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk drive (HDD), a solid state drive (SSD), a RAM, a ROM, an EPROM or Flash memory, an optical fiber, a portable compact disc read-only memory (CD-ROM), a digital versatile disc, an optical storage device, a magnetic storage device, or any suitable combination of the foregoing. In the context of this document, a computer-readable storage medium can be any tangible medium that can contain, or store a program for use by or in connection with an instruction execution system, apparatus, or device.

Program code embodied on a computer-readable medium can be transmitted using any appropriate medium, including but not limited to wireless, wireline, optical fiber, cable, RF, etc., or any suitable combination of the foregoing. Computer program code for carrying out operations for aspects of the present embodiments can be written in any combination of one or more programming languages, including an object-oriented programming language such as Java™, Smalltalk, C++ or the like and conventional procedural programming languages, such as the "C" programming language or similar programming languages. The program code can execute entirely on the user's computer, partly on the user's computer, as a stand-alone software package, partly on the user's computer and partly on a remote computer, or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider).

The terms "a" and "an," as used herein, are defined as one as or more than one. The term "plurality," as used herein, is defined as two or more than two. The term "another," as used herein, is defined as at least a second or more. The terms "including" and/or "having," as used herein, are defined as including (i.e., open language). The phrase "at least one of . . . and . . . " as used herein refers to and encompasses any and all possible combinations of one or more of the associated listed items. As an example, the phrase "at least one of A, B and C" includes A only, B only, C only, or any combination thereof (e.g., AB, AC, BC or ABC).

While the foregoing is directed to embodiments of the disclosed devices, systems, and methods, other and further embodiments of the disclosed devices, systems, and methods can be devised without departing from the basic scope thereof. The scope thereof is determined by the claims that follow.

What is claimed is:

1. An occupant bioprofiling system for determining biological aspects of occupants, comprising:
   one or more processors; and
   a memory communicably coupled to the one or more processors and storing:
      a biochemical detection module including instructions that when executed by the one or more processors cause the one or more processors to detect enclosure-related chemicals in an enclosure sample, the enclosure-related chemicals expelled by one or more occupants, and to collect one or more detectable markers for one or more of the enclosure-related chemicals;
      an association module including instructions that when executed by the one or more processors cause the one or more processors to correlate, using the detectable markers, one or more of the enclosure-related chemicals to an associated occupant of the one or more occupants; and
      a profiling module including instructions that when executed by the one or more processors cause the one or more processors to create a biological profile for the associated occupant, the biological profile comprising occupant-specific information derived from the enclosure-related chemicals.

2. The occupant bioprofiling system of claim 1, wherein the biochemical detection module further comprises instructions to screen out one or more infiltrating chemicals.

3. The occupant bioprofiling system of claim 1, wherein the biological profile is specific to the associated occupant.

4. The occupant bioprofiling system of claim 1, wherein biochemical detection module includes instructions to receive and store a biological sample.

5. The occupant bioprofiling system of claim 1, wherein the biological profile includes one or more disease states and a related profile signature.

6. The occupant bioprofiling system of claim 1, wherein the enclosure-related chemicals are collected over a period of time, and wherein the profiling module further comprises instructions to determine a temporal chemical variation, the temporal chemical variation providing a homeostatic association for the associated occupant.

7. The occupant bioprofiling system of claim 1, wherein the profiling module further comprises instructions to incorporate genetic information as part of the biological profile.

8. A bioprofiling vehicle, comprising:
   an air handling system; and
   a chemical detection device in fluid communication with the air handling system, the chemical detection device being configured to:
      detect enclosure-related chemicals in an enclosure sample, the enclosure-related chemicals expelled by one or more occupants;

collect one or more detectable markers for one or more of the enclosure-related chemicals;

correlate, using the detectable markers, one or more of the enclosure-related chemicals to an associated occupant of the one or more occupants; and create a biological profile for the associated occupant, the biological profile comprising occupant-specific information derived from the enclosure-related chemicals.

9. The bioprofiling vehicle of claim 8, wherein the bioprofiling vehicle further includes one of a biological collector in fluid communication with the chemical detection device and the air handling system, a chemical-selective filter positioned between and in fluid communication with the chemical detection device and the air handling system, a genetic material sampler positioned between and in fluid communication with the chemical detection device and the air handling system.

10. The bioprofiling vehicle of claim 8, wherein the biological profile is specific to the associated occupant.

11. The bioprofiling vehicle of claim 8, further comprising a biological collector, the biological collector in fluid communication with the air handling system and configured to receive and store a biological sample.

12. The bioprofiling vehicle of claim 8, wherein the bioprofiling vehicle comprises a chemical-selective filter, the chemical-selective filter configured to screen out one or more infiltrating chemicals from the enclosure sample.

13. The bioprofiling vehicle of claim 8, wherein the chemical detection device comprises a gas chromatograph and a mass spectrometer, the gas chromatograph and the mass spectrometer configured to detect the enclosure-related chemicals.

14. The bioprofiling vehicle of claim 8, wherein the biological profile includes one or more disease states and a related profile signature.

15. The bioprofiling vehicle of claim 8, wherein the enclosure-related chemicals are detected over a period of time to determine a temporal chemical variation, the temporal chemical variation providing a homeostatic association for the associated occupant.

16. The bioprofiling vehicle of claim 8, wherein the chemical detection device includes a genetic material sampler, the genetic material sampler configured to collect genetic material from the enclosure sample, and incorporate genetic information as part of the biological profile.

17. A non-transitory computer-readable medium for determining biological aspects of occupants and storing instructions that when executed by one or more processors cause the one or more processors to:

detect enclosure-related chemicals in an enclosure sample, the enclosure-related chemicals expelled by one or more occupants;

collect one or more detectable markers for one or more of the enclosure-related chemicals;

correlate, using the detectable markers, one or more of the enclosure-related chemicals to an associated occupant of the one or more occupants; and create a biological profile for the associated occupant, the biological profile comprising occupant-specific information derived from the enclosure-related chemicals.

18. The non-transitory computer-readable medium of claim 17, further comprising instructions to screen out one or more infiltrating chemicals from the enclosure-related chemicals.

19. The non-transitory computer-readable medium of claim 17, wherein the biological profile includes one or more disease states and a related profile signature.

20. The non-transitory computer-readable medium of claim 17, wherein the enclosure-related chemicals are detected over a period of time, and further comprising instructions to determine a temporal chemical variation, the temporal chemical variation providing a homeostatic association for the associated occupant.

\* \* \* \* \*